US005869036A

United States Patent [19]
Belshe et al.

[11] Patent Number: 5,869,036
[45] Date of Patent: Feb. 9, 1999

[54] LIVE ATTENUATED VACCINES BASED ON CP45 HPIV-3 STRAIN AND METHOD TO ENSURE ATTENUATION IN SUCH VACCINE

[75] Inventors: Robert B. Belshe; Ranjit Ray, both of St. Louis, Mo.

[73] Assignee: St. Louis University, St. Louis, Mo.

[21] Appl. No.: 569,853

[22] Filed: Dec. 8, 1995

[51] Int. Cl.[6] .............................. A01N 63/00; C12Q 1/70; C12Q 1/68; C12N 7/04
[52] U.S. Cl. .......................... 424/93.2; 424/93.1; 514/44; 435/235.1; 435/236; 435/5; 435/6
[58] Field of Search ................................ 424/93.1, 93.2; 435/69.3, 69.7, 5, 235.1, 6, 172.3, 236; 530/350, 395; 514/44

[56] References Cited

U.S. PATENT DOCUMENTS

| | | | |
|---|---|---|---|
| 3,927,209 | 12/1975 | Straub ........................................ | 424/89 |
| 4,215,107 | 7/1980 | Buynak et al. ............................ | 424/89 |
| 4,743,553 | 5/1988 | Rice et al. ................................ | 435/253 |
| 4,790,987 | 12/1988 | Compans et al. .......................... | 424/89 |
| 4,847,081 | 7/1989 | Rice .......................................... | 424/89 |
| 5,169,628 | 12/1992 | Wathen ...................................... | 424/89 |

OTHER PUBLICATIONS

Kevin Anderson et al., "Intracellular processing of the human respiratory syncytial virus fusion glycoprotein: amino acid substitutions affecting folding, transport and cleavage," 1992, pp. 1177–1188.
Robert B. Belshe et al., "Cold Adaptation of Parainfluenza Virus Type 3: Induction of Three Phenotypic Markers," 1982, pp. 10:235–242.
Robert b. Belshe et al., "Evaluation of a Live Attenuated Cold–Adapted Para–Infleunza Virus Type 3 Vaccine in Children," Aug., 1992, pp. 2064–2070.
H.N. Baybutt et al., "Molecular Cloning and Sequencing of F and 22K Membrane Protein Genes of the RSS–2 Strain of Respiratory Syncytial Virus," 1987, pp. 2789–2796.
Mary Lou Clements et al., "Evaluation of Bovine, Cold–Adapted Human, and Wild–Type Human Parainfluenza Type 3 Viruses in Adult Volunteers and in Chimpanzees," Jun. 1991, pp. 1175–1182.
Peter L. Collins et al., "Rescue of a 7502–Nucleotide (49.3% of Full–Length) Synthetic Analog of Respiratory Syncytial Virus Genomic RNA," 1993, pp. 252–256.
Galinski et al., "Molecular Cloning and Sequence Analysis of the Human Parainfluenza 3 Virus Gene Encoding the L Protein," 1988, pp. 499–510.
Galinski et al., "Molecular Cloning and Sequence Analysis of the Human Parainfluenza 3 Virus RNA Encoding the Nucleocapsid Protein," 1986, pp. 139–151.
Hall et al., "A Cold–Adapted Mutant of Parainfluenza Virus Type 3 is Attenuated and Protective in Chimpanzees," 1993, pp. 958–962.
Hu et al., "Molecular Cloning and Sequence Analysis of the Fusion Glycoprotein Gene of Human Parainfluenza Virus Type 2," 1990, pp. 915–920.

Johnson et al., "The A and B Subgroups of Human Respiratory Syncytial Virus: Comparison of Intergenic and Gene–overlap Sequences," 1988, pp. 2901–2906.
Johnson et al., "The Fusion Glycoproteins of Human Respiratory Syncytial Virus of Subgroups A and B: Sequence Conservation Provides a Structural Basis for Antigenic Relatedness," 1988, pp. 2623–2628.
Kawano et al., "Sequence of the Fusion Protein Gene of Human Parainfluenza Type 2 Virus and Its 3' Intergenic Region: Lack of Small Hydrophobic (SH) Gene," 1990, pp. 289–292.
Kuppuswamy et al., "Single nucleotide primer extension to detect genetic diseases: Experimental application to hemophilia B (factor IX) and cystic fibrosis genes," Feb., 1991, pp. 1143–1147.
Lawson et al., "Recombinant vesicular stomatitis viruses from DNA," May, 1995, pp. 4477–4481.
Lerch, et al., "Nucleotide Sequence Analysis and Expression from Recombinant Vectors Demonstrate That the Attachment Protein G of Bovine Respiratory Syncytial Virus Is Distinct from the of Human Respiratory Syncytial Virus," 1990 pp. 5559–5569.
Lopez et al., "Nucleotide sequence of the fusion and phosphoprotein genes of human respiratory syncytial (RS) virus Long strain: evidence of subtype genetic heterogeneity," 1988, pp. 249–262.
Martin–Gallardo et al., "Expression of the F Glycoprotein Gene from Human Respiratory Syncytial Virus in *Escherichia coli*: Mapping of a Fusion Inhibiting Epitope," 1991, pp. 428–432.
Martin–Gallardo et al., "Expression of the G glycoprotein gene of human respiratory syncytial virus in *Salmonella typhimurium*," 1993, pp. 453–458.
Merson et al., "Molecular cloning and sequence determination of the fusion protein gene of human parainfluenza virus type 1," 1988, pp. 97–105.
Precious, et al., "Sequence analysis of the HN gene of parainfluenza virus type 2," 1990, pp. 1163–1168.
Schnell et al., "Infectious rabies viruses from clone cDNA," 1994, pp. 4195–4203.

(List continued on next page.)

*Primary Examiner*—Jasemine C. Chambers
*Assistant Examiner*—Deborah J. R. Clark
*Attorney, Agent, or Firm*—Senniger, Powers, Leavitt & Roedel

[57] ABSTRACT

The present invention is based upon the observation that the temperature sensitive phenotype of the cp45 strain of HPIV-3 correlates to a mutation in the large, or L, gene of cp45 relative to the corresponding gene in the wild-type strain. This correlation enables new vaccines directed at viruses other than HPIV-3 by combining, through genetic engineering methods, the region of the cp45 viral genome which encodes proteins responsible for replication and internal structure with the region of the genome of the target virus which encodes proteins responsible for attachment, penetration and release of the virus and virus progeny, respectfully. Moreover, it is possible to determine whether HPIV-3 or a cp45-hybrid virus is attenuated by confirming the presence or absence of mutations in its L gene.

55 Claims, 6 Drawing Sheets

OTHER PUBLICATIONS

Spriggs et al., "Human parainfluenza virus type 3: messenger RNAs, polypeptide coding assignments, intergenic sequences, and genetic map," 1986, pp. 646–654.

Spriggs et al., "Sequence analysis of the P and C protein genes of human parainfluenza virus type 3: Patterns of amino acid sequence homology among paramyxovirus proteins," 1986, pp. 2705–2719.

Storey et al., "Structural Characterization of Viron Proteins and Genomic RNA of Human Parainfluenza Virus Type 3," 1984, pp. 761–766.

Sullender et al., "The respiratory syncytial virus subgroup B attachment glycoprotein: Analysis of sequence, expression from a recombinant vector, and evaluation as an immunogen against homologous and heterologous subgroup virus challenge," 1990, pp. 195–203.

Sullender et al., "Genetic diversity of the attachment protein of subgroup B respiratory syncytial viruses," 1991, pp. 5425–5434.

Walravens et al., "Sequence comparison between the fusion protein of human and bovine respiratory syncytial viruses," 1990, pp. 3009–3014.

Karron et al., "A Live Human Parainfluenza Type 3 Virus Vaccine is Attenuated and Immunogenic in healthy Infants and Children," 1995, pp. 1445–1450.

Ray et al., "Characterization of a Live, Attenuated Human Parainfluenza Type 3 Virus Candidate Vaccine Strain," 1995, pp. 1959–1963.

Robert B. Belshe, "textbook of Human Virology," 1991, pp. 388–407.

Crookshanks–Newman et al., "Protection of Wealing Hamsters from Experimental Infection With Wild–Type Parainfluenza Virus Type 3 (para 3) by Cold–Adapted Mutants of Para," 1986, pp. 131–137.

Galinski et al., "Molecular cloning and sequence analysis of the human parainfluenza 3 virus mRNA encoding the P and C proteins," 1986, pp. 46–60.

Kawano et al., "Sequence determination of the hemagglutinin–neuraminidase (HN) gene of human parainfluenza type 2 virus and the construction of a phylogenetic tree for HN proteins of all the paramyxoviruses that are infectious to humans," 1990, pp. 303–313.

Matsuoka et al., "Sequence of the hemagglutinin–neuraminidase gene of human parainfluenza virus type 1," 1990, pp. 107–113.

Stokes et al., "The complete nucleotide sequence of two–cold adapted, temperature sensitive attenuated mutant vaccine viruses (cp12 and cp45) derived from the JS strain of human parainfluenza virus type 3 (PIV 3)," 1993, pp. 43–52.

Bagai et al. J. of Virology. 69(11):6712–6719, Nov. 1995.

Palese [Trends in Microbiology, 3(4):123–125 (Apr. 1995)].

Castrucci et al [J of Virology 66(8):4647–4653 (Aug. 1992)].

FIG. 1 cp45

| | Nucleotide | | | Amino Acid | |
|---|---|---|---|---|---|
| Location | | Change | Location | | Change (wt -» cp45) |
| 23 | | T » C | | | |
| 24 | | C » T | | | |
| 28 | | G » T | | | |
| 334 | TCC » TCT | | | | |
| 376 | AAT » AAC | | | | |
| 627 | CCC » ACC | 199 | | Pro -» Thr |
| 658 | AAC » AAT | | | |
| 1451 | ATA » GTA | 155 | | Ile -» Val |
| 1541 | GCA » ACA | 420 | | Ala -» Thr |
| | | | 450 | | |
| 115 | GGT » GGC | | | |
| 1224 | GTT » GCT | 14 | | Val -» Ala |
| 700 | TAT » TAC | | | |
| 1348 | GAA » GAG | | | |
| 2698 | TCA » TCG | 384 | | |
| 2846 | TAC » CAC | 226 | | |
| 2998 | TTG » TTT | 442 | | |
| | | | 892 | | Tyr -» His |
| | | | 942 | | Leu -» Phe |
| | | | 992 | | |
| 3958 | TTC » TTT | 1312 | | |
| 4695 | ACT » ATT | 1558 | | Thr -» Ile |

LEADER — NP — P — M — F — HN — L — TRAILER

LIVE ATTENUATED VACCINES BASED ON CP45 HPIV-3 STRAIN AND METHOD TO ENSURE ATTENUATION IN SUCH VACCINE

Funding for research supporting this invention was provided, in part, by the U.S. Department of Health and Human Services. The U.S. Government may have certain rights in this invention.

BACKGROUND OF THE INVENTION

The present invention relates to enveloped, negative-sense, single-stranded RNA viruses and to the use of such viruses as live attenuated vaccines. Specifically, the invention relates to new human vaccines for enveloped viruses such as parainfluenza, respiratory syncytial virus, measles and influenza viruses, among others. The invention also relates to a method for screening such vaccines to ensure temperature sensitive attenuation prior to their administration and to check the stability of the attenuated strain after administration.

A number of viruses may cause severe infections in humans and animals. For example, respiratory syncytial virus (RSV) and parainfluenza virus are two of the leading causes of severe upper and/or lower respiratory tract disease in neonates and young infants. Other viruses, such as influenza virus, measles virus and human immunodeficiency virus, are also of significant concern.

A variety of vaccines have been developed over the years to prevent viral infections in animals and humans. Two principle types of vaccines have been used: killed viruses and attenuated live virus. A killed virus is typically inactivated by chemical or physical treatment, but is generally less effective in stimulating a lasting immune response than an attenuated live virus. Attenuated live viruses are typically more effective, but may revert back to their virulent state while in the body. The time and cost involved in developing either killed or live vaccines is significant.

Live, attenuated vaccines may be obtained directly from progeny viruses isolated from infected animals. For example, U.S. Pat. No. 3,927,209 to Straub discloses a parainfluenza type-3 vaccine isolated as a virus strain from a bovine respiratory tract. Live attenuated vaccines may also be obtained by repeatedly cold passaging a wild-type strain through suitable cultures until the virus has lost its original pathogenic properties. For example, cp45, a cold-adapted, temperature sensitive strain was obtained by passing the wild-type virus (JS strain) of HPIV-3 45 times at reduced temperatures. (Belshe and Hissom, 1982). The temperature sensitive cp45 strain is currently under evaluation for use as a candidate vaccine in humans. (Karron et al. 1995; Hall et al. 1993; Belshe et al. 1992; Clements et al. 1991; Crookshanks-Newman and Belshe 1986). Recent evaluation in children has revealed the cp45 strain to be highly attenuated and effective in stimulating immunogenic response. (Karron et al. 1995; Belshe et al. 1992).

Attenuation in a particular vaccine strain is commonly evaluated with respect to three phenotypes of the strain: cold adaptation, temperature sensitivity and plaque size or yield in tissue culture. Cold adaptation relates to the ability of the virus to grow at 20° C. and the temperature sensitivity relates to whether such growth is inhibited at temperatures of around 40° C. Plaque titers are an assay for quantitatively evaluating the extent of virus growth, and are commonly used to evaluate the extent of cold-adaptive and/or temperature sensitive phenotypes. Other methods for determining whether a vaccine is attenuated involve administering the vaccine to primates. For example, new polio vaccine lots are typically administered to monkeys before being approved for sale by the FDA.

A continuing need exists for developing new vaccines. The prior art methods of developing live attenuated vaccines by cold passaging, while often effective, are not predictable as to their success, and are necessarily limited to application against a single virus. A need also exists for alternative methods to determine whether a virus is sufficiently attenuated. Characterization of cold adaptive and temperature sensitive phenotypes are not definitive. Administration of vaccines to test animals are likewise not definitive, and are inefficient.

SUMMARY OF THE INVENTION

It is therefore an object of the invention to develop vaccines which are suitable for use against a variety of viruses. It is a further object of the invention to make such vaccines using genetic engineering technology. It is likewise an object to more specifically determine whether a virus strain is attenuated.

Briefly, therefore, the present invention is directed to a live, attenuated vaccine, suitable for use in humans or animals. The vaccine comprises an enveloped, negative-sense, single-stranded RNA virus. The virus has a genome which includes a nucleic acid sequence that encodes at least one surface antigen of a target virus and a nucleic acid sequence which encodes a variant protein which is a HPIV-3 L protein that is different in amino acid sequence from the L protein of wild-type HPIV-3. The surface antigen of the target virus is different from the surface antigens of cp45. The vaccine also comprises a pharmaceutically appropriate carrier.

The present invention is likewise directed to a vaccine which comprises an enveloped, negative-sense, single-stranded RNA virus, where the virus has a genome which comprises, in succession from its 3' end: (i) a nucleic acid sequence which is the same as the nucleic acid sequence of the 3' leader region of the cp45 viral genome; (ii) a nucleic acid sequence which encodes the nucleocapsid protein, [NP], of cp45; (iii) a nucleic acid sequence which encodes the phosphoprotein, P[+C], of cp45; (iv) a nucleic acid sequence which encodes the matrix protein, [M], of cp45; (v) a nucleic acid sequence which encodes at least one surface protein of a target virus; and (vi) a nucleic acid sequence which encodes a variant protein which differs in amino acid sequence from the L protein of wild-type HPIV-3. The target virus is either HPIV-1, HPIV-2 or RSV and the surface protein of the target virus is different from the surface proteins of cp45. The variant protein has at least two variations in amino acid sequence relative to the wild-type HPIV-3 L protein: His for Tyr at residue 942 of SEQ ID NO:1 and Phe for Leu at residue 992 of SEQ ID NO:1. The vaccine also includes a pharmaceutically appropriate carrier.

The invention is directed as well to a cp-45 hybrid virus which is suitable for use as a vaccine in humans or animals. The virus comprising an enveloped, negative-sense, single-stranded chimeric RNA genome, which includes, in succession from its 3' end: (i) a nucleic acid sequence which is the same as the nucleic acid sequence of the 3' leader region of cp45 viral genome; (ii) a nucleic acid sequence which encodes the nucleocapsid protein, [NP], of cp45; (iii) a nucleic acid sequence which encodes the phosphoprotein, P[+C], of cp45; (iv) a nucleic acid sequence which encodes the matrix protein, [M], of cp45; (v) a nucleic acid sequence which encodes at least one surface antigen of a target virus;

and (vi) a nucleic acid sequence which encodes a variant protein which is different from the L protein of wild-type HPIV-3. The surface antigen of the target virus is different from the surface antigens of cp45.

The invention is directed, moreover, to a method for producing an enveloped, negative-sense, single-stranded RNA virus suitable for use as a live, attenuated human or animal vaccine. A host cell is transfected with a plasmid vector that comprises a chimeric genome. The genome includes a nucleic acid sequence which encodes at least one surface antigen of a target virus and a nucleic acid sequence which encodes a variant protein, the variant protein being a HPIV-3 L protein which is different from the L protein of wild-type HPIV-3. The surface antigen of the target virus is different from the surface antigens of cp45. The host cell is cotransfected with plasmid vectors that express HPIV-3 NP, P and L proteins. The cotransfected host cell is incubated to produce a cp-45 hybrid virus and the hybrid virus is isolated in a pharmaceutically acceptable carrier to form a vaccine.

The invention is similarly directed to a plasmid vector comprising a chimeric RNA genome. The positive-sense or negative-sense RNA genome includes a nucleic acid sequence which encodes at least one surface antigen of a target virus, the surface antigens being different from the surface antigens of cp45, and a nucleic acid sequence which encodes a variant protein, the variant protein being a HPIV-3 L protein which is different from the L protein of wild-type HPIV-3.

The invention is furthermore directed to a method for determining whether a HPIV-3 or a cp45-hybrid virus is attenuated. The method comprises confirming the presence of at least one variation in the genome of the virus relative to the genome of wild-type HPIV-3. The variation is in the region of the genome which encodes the L protein.

The present invention is also directed to a method for determining whether a virus has a temperature sensitive phenotype. A sample of HPIV-3 or a cp45-hybrid virus is obtained and a first plaque assay is performed. A host cell is transfected with a plasmid vector that expresses wild-type HPIV-3 L protein and infected with the virus. After incubating, a second plaque assay is performed and compared to the first plaque assay.

The invention offers new opportunities for producing live vaccines which can be used in conjunction with a variety of viruses. Because the vaccines of the present invention will have the same temperature sensitive phenotype as exhibited by cp45, such vaccines will be attenuated during use in humans. Furthermore, the invention provides a direct and efficient method for determining temperature sensitive phenotype and attenuation in HPIV-3 viruses and in cp45 hybrid viruses.

Other features and objects of the present invention will be in part apparent to those skilled in the art and in part pointed out hereinafter.

BRIEF DESCRIPTION OF THE DRAWINGS

FIG. 1 is a schematic representation of the HPIV-3 viral genome, shown vertically 5' (top) to 3' (bottom) in its cDNA sense. The position number for nucleotide changes in the leader region correspond to their position in relation to the genome, whereas all other position numbers refer to the position of nucleotide changes within the individual gene.

FIG. 2(a) shows cDNA after 15 cycles of PCR amplification from wild-type HPIV-3 (lane 1), cp45 (lane 2) and plasmid DNA containing the P gene (lane 3). FIG. 2(b) depicts the results of a slot blot hybridization analysis using phosphorImaging.

FIG. 3(a) shows cell lysates immunoprecipitated with Rabbit anti-HPIV-3, and FIG. 3(b) shows cell lysates immunoprecipitated with pooled monoclonal antibodies to HN and NP of wild-type HPIV-3.

DETAILED DESCRIPTION OF THE INVENTION

Figures 2A, 2B:
FIGS. 2(a) and 2(b) depict the results of Southern hybridization or southern blot analysis, comparing mRNA levels of P protein gene between cp45 and wild-type HPIV-3.

As used herein, the term "HPIV-3" includes all HPIV-3 strains, including wild-type HPIV-3 and attenuated strains such as cp45. "Wild-type HPIV-3" refers to HPIV-3 (JS) strain. (Belshe and Hissom 1982). The term "cp45" refers to the attenuated, temperature sensitive cp45 strain of wild-type HPIV-3.

The present invention is based upon the observation that the temperature sensitive phenotype of the cp45 strain of HPIV-3 is caused by a mutation in the large, or L, gene of cp45 relative to the corresponding gene in the wild-type strain. Without being bound by any theory, the L gene is believed to encode the RNA-dependent RNA polymerase of HPIV-3 and the temperature sensitive phenotype is believed to arise due to a decrease in the polymerase activity at higher temperatures, generally greater than or equal to about 37° C. Such decreased polymerase activity results in reduced transcription of the viral RNA. Hence, it is now understood that a significant level of attenuation in the cp45 strain of HPIV-3 is associated with the mutant L gene. Specifically, it is believed that higher temperatures result in cellular pH changes which cause conformational changes in the mutant RNA-dependent RNA polymerase, and such conformational changes decrease its activity, which in turn results in reduced replication of the virus. The wild-type RNA-dependent RNA polymerase does not appear to undergo such temperature sensitive conformational changes.

The correlation of the temperature sensitive phenotype of cp45 to its L gene enables several practical applications. For example, it is now possible to create new vaccines directed at viruses other than HPIV-3 by combining, through genetic engineering methods, the region of the cp45 viral genome which encodes proteins responsible for replication and internal structure with the region of the genome of the target virus which encodes proteins responsible for attachment, penetration and release of the virus and virus progeny, respectfully. Moreover, it is possible to determine whether an HPIV-3 strain, or a hybrid virus strain made by the aforementioned method, is attenuated by confirming the presence or absence of mutations in its L gene. A verification of attenuation is desirable before administration as a check of new vaccine lots and also after such administration to ensure the stability (i.e., non-reversion) of the vaccine virus.

HPIV-3 is an enveloped, negative-sense, single-stranded RNA virus. Its viral genome encodes at least six structural proteins, including, in succession from the 3' end: [3'-NP-P(+C)-M-F-HN-L-5'], wherein 3' refers to the 3' leader region of the genome and wherein NP, P(+C), M, F, HN, and L refer to the regions of the genome which encode the nucleocapsid protein, the phosphoprotein, the matrix protein, the fusion protein, the hemagglutinin-neuraminidase protein, and the large protein, respectively. (Spriggs and Collins 1986; Storey et al 1984). Relatively short, non-coding intergenic regions separate each of the regions encoding functional proteins.

The nucleocapsid protein, NP, is the most abundant structural protein. It encapsidates the genomic RNA and is believed to maintain the structural integrity and template function of the genome. The L protein functions as the RNA-dependent RNA polymerase, and the P protein functions as an auxiliary regulatory protein which supports the function of L. The P(C+) gene also contains a (C+) reading frame. The matrix, fusion, and hemagglutinin-neuraminidase proteins, M, F and HN, respectively, collectively form the lipid envelope which surrounds the nucleocapsid core. M forms the structural internal portion of the envelope, while F and HN are surface glycoproteins. The H portion of the HN protein and the F protein are responsible for attachment onto and penetration into a host cell by HPIV-3, while the N portion of the HN protein is responsible for release of the progeny viruses from the host cell after replication.

During reproduction of paramyxoviruses such as HPIV-3 in the cytoplasm of infected cells, the nucleocapsid (RNA-NP) serves as a template for transcription by the viral RNA polymerase, L. L and P proteins are both associated with the RNA-NP core, and during primary transcription, the L-P complex interacts with the nucleocapsid core to transcribe the genomic RNA into individual mRNAs which code for viral proteins. In addition, during replication in an infected cell, NP may form a soluble complex with P. This complex is thought to interact with transcribing nucleocapsid complexes to switch from primary transcription to replication of the viral RNA.

The complete nucleic acid sequences of the wild-type HPIV-3 genome and of the temperature sensitive cp45 genome are known and have been compared. (Stokes et al. 1993; Galinski et al. 1988; Galinski et al. 1986; Galinski et al. 1986'; Spriggs and Collins 1986; Spriggs and Collins 1986'; Storey et al. 1984). The known amino acid sequences of the L protein of wild-type HPIV-3 (JS) strain and of cp45 are shown herein as SEQ ID NO:1 and SEQ ID NO:2, respectively. At least 18 nucleotide differences exist between wild-type HPIV-3 genome and the cp45 genome, as shown in FIG. 1. However, nine of these 18 nucleotide changes are found in non-attenuated strains or do not result in amino acid changes in the proteins which they encode. Two of the remaining changes are in the non-coding 3' leader region, but may be important for regulation. Hence, at least seven remaining nucleotide differences between the cp45 genome and the wild-type genome are known to result in amino acid sequence changes in four variant proteins: M, F, HN and L. The changes in amino acid sequences of the variant cp45 proteins relative to the corresponding wild-type proteins include: in the M gene, substituting threonine (Thr) for proline (Pro) at residue 199; in the F gene, substituting valine (Val) for isoleucine (Ile) at residue 420 and threonine (Thr) for alanine (Ala) at residue 450; in the HN gene, substituting alanine for valine at residue 384; and in the L gene, substituting histidine (His) for tyrosine (Tyr) at residue 942, of SEQ ID NO:1 phenylalanine (Phe) for leucine (Leu) at residue 992 of SEQ ID NO:1 and isoleucine (Ile) for threonine (Thr) at residue 1558 of SEQ ID NO:1.

The variations in the region of the wild-type HPIV-3 genome which encodes the L protein are now understood to directly correlate to the temperature sensitive phenotype of the cp45 strain. Specifically, the variant L protein has been linked to decreased transcription of the cp45 virus at non-permissive temperatures. Some reduction in transcriptional activity is observed beginning at about 37° C., and a marked reduction occurs at or above about 38° C. Hence, the non-permissive temperatures for cp45 are considered to be temperatures greater than about 37° C., and generally ranging from about 37° C. to about 40° C.

Without being bound by theory, the His and Phe substitutions in the L protein, at residues 942 and 992, SEQ ID NO:1, respectively, are believed to be important contributors to the presence of the temperature sensitive phenotype. Histidine-phenylalanine interactions are pH dependent, and intracellular pH changes are affected by temperature. A shift to the higher non-permissive temperatures and a corresponding change in pH results in histidine-phenylalanine interactions which cause conformational changes in the RNA dependent RNA polymerase (L protein). Such conformational changes, in turn, result in a decreased activity of the polymerase and a corresponding decrease in transcription and replication. The wild-type RNA-dependent RNA polymerase is not believed to undergo such temperature sensitive conformational changes.

The temperature-dependent replication of the cp45 strain clearly contributes to the observed attenuation in the cp45 vaccine. As shown in Table 1, replication of the temperature sensitive cp45 strain is reduced by a factor of about $10^6$ as compared to replication of the wild-type ("WT") strain. (See Example 1). Referring again to Table 1, cp45 showed some replication upon shifting the incubation temperature from 39.5° C. to 32° C. after 24 hours at the higher temperature, and hence demonstrated the characteristic temperature-sensitive phenotype. The poor transcriptional activity of the cp45 virus strain results in markedly reduced mRNA synthesis at 39.5° C., and as a result, protein synthesis and virus growth are significantly affected. (See Example 1). Other factors also contribute to attenuation, but to a relatively minor extent. For example, as shown in Table 2, a decrease in neuraminidase activity also results during a shift to higher temperatures. (See Example 2). However, while the decrease in neuraminidase activity likely restricts the release of the progeny virus particles from the infected cell surface, the decrease in activity by a factor of less than 10 suggests that it is not the major factor in the observed attenuation of cp45. Nucleotide changes in the 3' leader region of cp45 relative to the wild-type strain are also suspected of affecting the cold adaptive, temperature sensitivity and/or attenuation properties of cp45.

TABLE 1

Comparison of yields of cp45 and parent wild-type (WT) viruses in a temperature-shift experiment

| Virus Strain | Incubation Temp (°C.) | Virus yield[a] |
|---|---|---|
| cp45 | 32 | $2.9 \times 10^7$ |
| WT | 32 | $1 \times 10^7$ |
| cp45 | 39.5 | $1.2 \times 10$ |
| WT | 39.5 | $8 \times 10^6$ |

TABLE 1-continued

Comparison of yields of cp45 and parent wild-type
(WT) viruses in a temperature-shift experiment

| Virus Strain | Incubation Temp (°C.) | Virus yield[a] |
|---|---|---|
| cp45 | 39.5 →32[b] | $2 \times 10^3$ |
| WT | 39.5 →32[b] | $1.5 \times 10^7$ |

[a]Virus yields in L-132 cells, infected at similar multiplicities of infection, are expressed after 48 h of incubation.
[b]Temperature shift.

TABLE 2

Comparison of neuraminidase activities of cp45 and
parent wild-type (WT) viruses

| Virus strain | Incubation temp (°C.) | HA units used | Neuraminidase activity with[a]: Fetuin | Neuraminlactose |
|---|---|---|---|---|
| WT | 39.5 | 512 | 0.24 | 3.60 |
| cp45 | 39.5 | 512 | 0.03 | 0.83 |
| WT | 32 | 2,048 | 1.11 | 2.30 |
| cp45 | 32 | 2,048 | 0.67 | 2.30 |

[a]Results are presented as optical density values at 549 nm.

Although the transcriptional activity of cp45 is reduced relative to wild-type HPIV-3, other biological properties were not significantly altered. The antigenic sites of the envelope glycoproteins, defined by reactivity to a panel of monoclonal antibodies remained unaffected in cp45 as compared to the wild-type strain. (See Example 3). Similarly, transport of HN and F glycoproteins to the cell surface, and functional activity of HN, as determined by an HA assay test, demonstrated no substantial differences between the properties of the cp45 strain relative to the wild-type strain. (See Example 3). Further, limited viral morphogenesis occurred at the nonpermissive temperature.

The temperature dependent activity of the cp45 RNA-dependent RNA polymerase (L protein) and the corresponding reduced transcription of cp45 at non-permissive temperatures (about 40° C.) is associated with variations in the region of the viral genome which encodes the L protein. Whereas a cell infected with cp45 alone does not replicate significantly, cells which were co-transfected with cp45 and a recombinant DNA vector which expressed wild-type L protein showed significant levels of replication. (See Examples 4 and 5).

Table 3 reports virus replication yields of plaque assays done on L-132 cells. Briefly, CV-1 cells were cotransfected with plasmid DNA (pRSV-T) encoding the SV40 large T antigen and the recombinant plasmid DNAs (L, P, and/or NP). The CV-1 cells were then infected with cp45 virus at 20 hours posttransfection and incubated at 39.5° C. for 28 hours.

As shown in Table 3, when the temperature sensitive cp45 strain is complemented by non-mutant wild-type L protein in a complementation assay, the level of replication, as measured by plaque assay methods, increased by a factor of more than 100 relative to the uncomplemented cp45. In contrast, complementation of the cp45 strain with wild-type P protein or with wild-type NP protein had no effect on replication. Cells cotransfected with cp45 and with wild-type L and P proteins, or with wild-type L, P and NP proteins, showed similar increases in yield over cells cotransfected with cp45 and wild-type L protein alone, thereby indicating the key role of the L protein. The recovery of cp45 replication at higher, non-permissive temperatures by complementing the cp45 strain with wild-type L protein demonstrates that the variant L protein (RNA-dependent RNA polymerase) is responsible for the temperature sensitive phenotype of cp45.

TABLE 3

Complementation assay for recovery of cp45 virus at
the nonpermissive temperature (39.5° C.)

| Gene(s) used in complementation[a] | Virus recovery titer (PFU/ml of culture medium) at 32° C.[b] |
|---|---|
| None | <1.0 |
| L, P, and NP | $2.3 \times 10^3$ |
| L and P | $1.9 \times 10^2$ |
| L | $3.3 \times 10^2$ |
| P | <1.0 |
| NP | <1.0 |

Importantly, cp45 progeny virus produced from co-transfected cells in which wild-type L protein was used to complement the cp45 strain at non-permissive temperatures retained the temperature sensitive phenotype of the parent cp45 strain. (See Example 6). Further, the L protein complementation of cp45 is heterotypically exclusive. (See Example 6).

The observation that the temperature sensitive phenotype and the associated attenuation of the cp45 strain of HPIV-3 is caused by a variation in the L gene of cp45 enables a method for producing vaccines for other viruses, such other viruses referred to herein as target viruses. Target viruses include any enveloped virus that has one or more surface antigen. Surface antigens include surface proteins and/or surface glycoproteins. As used herein, the term surface antigen refers to proteins, such as glycoproteins, and other moieties which are responsible for the attachment of the viruses onto host cells, which allow the viruses to penetrate into the host cells to establish infection, and/or which facilitate release of progeny virus from the infected host cells.

Hence, in addition to related enveloped, negative-sense, single-stranded RNA viruses such as human parainfluenza virus type 1 (HPIV-1), human parainfluenza virus type 2 (HPIV-2), respiratory syncytial virus (RSV), human influenza virus type A, human influenza virus type B, and measles viruses, target viruses would also include other enveloped viruses, such as paramyxoviruses, orthomyxoviruses, retroviruses (e.g. human immunodeficiency viruses HIV-GP120 and HIV-GP41), arenaviruses, coronaviruses, bunyaviruses, rhabdoviruses, togaviruses, herpesviruses, poxviruses and hepadnaviruses. Preferable target viruses include enveloped viruses which reproduce in the cytoplasm. The target virus of the present invention may be specific to humans, specific to animals or common to both animals and humans. Bovine RSV and cattle HPIV-3 (shipping fever virus) are typical animal viruses included within the scope of the present invention.

The gene sequence which encodes the surface glycoproteins of a target virus may be substituted for the corresponding sequence in the cp45 genome which codes for the HN and F proteins, to result in a hybrid virus. That is, the region of the genome of the target virus that encodes one or more surface glycoproteins may be combined with the regions of the cp45 genome related to replication and internal structure of the virus. The resulting hybrid virus will have the temperature sensitive attenuation properties contributed by the cp45 genome and the virus-specific antigenic properties of the virus from which the surface glycoproteins are contributed. As such, the hybrid virus should have a predictable level of safety and immunogenicity and be suitable for use as a vaccine in humans.

A vaccine developed from cp45 in combination with a target wild-type virus would comprise an enveloped, negative-sense, single-stranded RNA hybrid virus. A preferred hybrid virus would have a chimeric genome which comprises, in succession from its 3' end: a nucleic acid sequence which is the same as the nucleic acid sequence of the 3' leader region of a cp45 viral genome; nucleic acid sequences which encode the nucleocapsid protein, [NP], the phosphoprotein, P[+C], and the matrix protein, [M], of cp45; a nucleic acid sequence which encodes at least one surface antigen (e.g. surface protein or surface glycoprotein) of an enveloped target virus, and a nucleic acid sequence which encodes a variant protein which is different from the L protein of wild-type HPIV-3.

An alternative, but presently less preferred hybrid virus would have a genome which includes a 3' leader region, a NP region, a P[+C] region and a M region, where one or more of these regions are the same as the corresponding regions of the wild-type HPIV-3 strain. The genome of such a hybrid virus would also include a region encoding the surface glycoproteins of the target virus and a region which encodes a variant of the wild-type L protein. Because such a hybrid virus would differ from wild-type HPIV-3 only with respect to its gene encoding surface glycoproteins and its L gene, the possibility for reversion to a non-attenuated strain is higher than if the genome of the hybrid virus more closely resembles the cp45 genome in the regions encoding the NP, P[+C] and M proteins and in the 3' leader region.

In addition to an attenuated hybrid virus, the vaccine of the present invention also comprises a pharmaceutically appropriate carrier for the attenuated hybrid virus. Typical carriers include the tissue culture fluid in which the virus is grown, dilutents such as phosphate-buffered saline and/or stabilizers such as gelatin.

The variant protein preferably has at least one or more variations in amino acid sequence relative to the wild-type protein. The variations in amino acids preferably include substitution of His for Tyr at residue 942, of SEQ ID NO:1, Phe for Leu at residue 992 of SEQ ID NO:1 and Ile for Thr at residue 1558 of SEQ ID NO:1. More preferably, the variant protein has at least two variations in amino acid sequence relative to the wild-type HPIV-3 L protein: a substitution of His for Tyr at residue 942 of SEQ ID NO:1 and a substitution of Phe for Leu at residue 992 of SEQ ID NO:1. The variant protein most preferably has all three of the variations in amino acid sequence of the cp45 L protein, and may include other variations as well.

The method for producing an attenuated hybrid virus suitable for use as a human vaccine against a target wild-type virus includes genetic engineering techniques applied to insert target gene sequences encoding target surface glycoproteins into the cp45 genome in place of the corresponding surface glycoprotein genes in the cp45 genome. The method detailed below is a preferred method. However, those skilled in the art will appreciate that variations in this method and other methods are also suitable to produce a hybrid virus. Example 7 details methods for producing attenuated hybrid vaccines for target viruses HPIV-1, HPIV-2, RSV, influenza viruses and measles viruses.

To produce a cp45 hybrid virus, the viral genome of cp45 is first converted into full-length cDNA clone. Typically, several different portions of the genome are amplified using PCR and ligated in successive steps into a full length cDNA clone. The regions of the target virus genome encoding the target's surface glycoproteins are also converted into a cDNA clone. Target viruses having negative-sense or positive-sense, single-stranded RNA genomes, such as HPIV-1, HPIV-2, RSV, measles and influenza viruses, are converted in the same manner as cp45. Viruses with DNA genomes can be directly ligated into the DNA plasmid vector.

The cDNA clone of the cp45 genome is then incorporated into a plasmid vector. Plasmid vectors such as pBluescriptII (Stratagene) or other commercially available vectors which are suitable for subsequent transfection and expression in a mammalian host cell may be used. Briefly, the cDNA clone and plasmid vector are combined using restriction enzyme digestion and ligation reactions. The recombinant plasmid is then cloned and purified.

Genetic manipulations are conducted to replace the regions of the cp45 cDNA genome which encode the F and HN proteins with the cDNA copy of the target virus' genes which encode the target's one or more surface glycoproteins.

The negative-sense, single-stranded RNA hybrid virus is then recovered from the cDNA genome by transfecting the hybrid cDNA plasmid vector into mammalian cells for synthesis of progeny viral genome and viral proteins using reverse genetic techniques. (Palese 1995; Lawson et al. 1995; Schnell et al. 1994). Briefly, the plasmid vector containing the cDNA copies are transfected into a host cell which has been previously infected with a recombinant vaccinia virus expressing bacteriophage T7 RNA polymerase. Plasmid vectors that express HPIV-3 NP, P and L proteins, produced according to the method described in Example 4, are cotransfected into the host cell. The cDNA is transcribed to produce full-length, negative-sense (genomic) RNA. Expression of the NP, L and P proteins facilitate synthesis of progeny hybrid virus. The hybrid virions are then isolated, grown in appropriate mammalian cells and tested to verify temperature sensitive phenotype and associated attenuation.

The observation that the temperature sensitive phenotype and the associated attenuation of the cp45 strain of HPIV-3 is caused by a variation in the L gene of cp45 also enables a method for determining whether a HPIV-3 strain is attenuated. Such a determination is made by confirming the presence of at least one variation in the region of the HPIV-3 strain genome encoding the L protein relative to the corresponding region of the genome of wild-type HPIV-3. A determination can, in the same manner, also be made as to whether a cp45-hybrid virus is attenuated.

Verification of attenuation is necessary in a variety of situations. For example, verification is useful in research laboratories, as quality control checks in commercial production of vaccines, as verification by regulatory agencies, and as final checks on new vaccine lots before administration to a patient. Verification of attenuation is likewise useful to check the stability of a vaccine after it has been administered to a patient. Isolates from the patient may be checked to verify that the progeny virus have retained the temperature sensitive attenuated phenotype.

A variety of methods for confirming the presence of nucleotide variations are known in the art. For example, while cumbersome, the genome which encodes the L protein could be sequenced in its entirety and compared to the wild-type gene for L. Alternatively, where the viral strain being tested is cp45 or a cp45 hybrid virus, the L gene could be cut with restriction enzymes near the expected variations at residues 942, 992 and 1558, and the smaller fragments could be sequenced for comparison with the L gene of wild-type HPIV-3 or of cp45. A more preferred method would include isolating the viral strain being tested in single-stranded form, hybridizing the viral genome to probes which flank the variations, amplifying the region between the probes using PCR and sequencing the amplified regions of the L gene for comparison to wild-type HPIV-3 or to cp45. Other alternatives for determining point variations in gene sequences, such as single nucleotide extension reactions (Kuppuswamy et al. 1991) are also known in the art.

The complementation assay of the present invention, described in detail in Examples 3 and 4, may also be used to confirm the presence of at least one variation in the L gene. This method not only verifies gene sequence variation, but also simultaneously verifies the functional effect of such variations in the L gene. The dual nature of such a test is advantageous over sequencing information alone, due to the possibility of suppressor mutations.

Briefly, a viral strain sample is obtained from a new vaccine lot or as a purified patient isolate. If necessary, the sample is amplified by growing in a cell culture medium. A standard, first plaque assay is performed, as a control, by incubating at a non-permissive temperature (about 40° C.), and measuring replication. A complementation assay is then performed in which host cells are transfected with a plasmid vector that expresses wild-type HPIV-3 L protein and are also infected with the viral sample. (See Examples 3 and 4). Plasmid vectors which express wild-type NP and/or P proteins may be cotransfected into the host cells. A second plaque assay is performed on the complemented viral sample, and the results are compared to the results of the first plaque assay. A variation in the sample virus's L gene will be indicated by a significant increase, preferably at least a 10 fold increase, and most preferably a 100 fold increase, in replication of the complemented viral sample as compared to the non-complemented sample, as measured by plaque assays.

The following examples illustrate the principles and advantages of the invention.

EXAMPLES

As used in the following examples, cp45 was derived from wild-type HPIV-3 (JS strain), an isolate originally cultured from a child with febrile respiratory disease. A cold-adapted mutant was selected after serial passage of the virus 45 times at 20° C. and isolated by plaque purification (Belshe and Hissom 1982). The cp45 virus was subsequently grown at 32° C. in continuous cell lines.

Example 1

Temperature-Dependent Replication, Protein Synthesis and mRNA Synthesis of cp45

Unlike the wild-type HPIV-3 strain, the cp45 strain loses its replication ability at non-permissive higher temperatures (above about 37° C.). This loss of replication activity contributes to the observed attenuation in the cp45 vaccine. Moreover, a related decrease in virus-specific mRNA synthesis and in protein synthesis exists in the cp45 strain relative to the wild-type strain.

cp45 virus was absorbed into a cellular culture medium at 32° C. for 1 hour and grown at 39.5° C. for 24 hours. Infected cells were then shifted to 32° C. for growth for an additional 24 hours. The virus titer in the culture supernatant was determined by plaque assay in L-132 cells. Infected cell monolayers were either stained with hematoxylin-eosin Y or overlaid with 0.9% agar and 0.005% neutral red for visualization of viral plaques. The results from at least three independent experiments showed consistent virus recovery (less than fivefold variation).

Comparison of cp45 and wild-type (JS) virus replication in L-132 cells at permissive (32° C.) and nonpermissive (39.5° C.) temperatures in a temperature-shift assay is shown in Table 1. Normal growth of both viruses was observed at the permissive temperature. However, poor replication (reduction of ~$10^6$-fold) of cp45 was observed when the virus was absorbed on L-132 cells at 39.5° C. and incubated at the same temperature. However, the virus showed some replication upon changing the incubation temperature from 39.5° to 32° C. after 24 h. On the other hand, the wild-type virus exhibited similar replication at 39.5° and 32° C. cp45 virus replicated upon temperature shift from 39.5° to 32° C. demonstrated the characteristic temperature-sensitive phenotype, thereby indicating an absence of the revertant virus at 39.5° or 32° C.

The virus-specific RNA synthesis occurring in the cp45 strain is likewise significantly lower than such synthesis in the wild-type strain. Hence, only low levels of messenger RNA (mRNA) are produced at the non-permissive temperature. In order to determine the overall viral transcriptional activity at the nonpermissive temperature, mRNA synthesis from the P protein gene of cp45 virus was studied by reverse transcription-PCR for comparison with that of the wild-type virus.

Briefly, L-132 cells were infected with cp45 or wild-type virus at a similar multiplicity of infection. After virus absorption at 32° C., cells were grown at 39.5° C. for 24 h. Infected cells were treated with actinomycin D (10 μg/ml) for 14 h, and RNA was prepared by acid guanidinium thiocyanate-phenol-chloroform extraction. Amplification of the P mRNA was done by reverse transcription-PCR from the same quantities of total RNA (10 μg) and virus-specific sense (CCAACAACAACTCCCAGATC, nucleotide positions 2740 to 2759) and anti-sense (TGCCTCCATAAGTGGGTCAA, nucleotide positions 3280 to 3299) synthetic oligonucleotide primers. The amplification reaction was performed by using an automatic thermocycler (Perkin-Elmer Cetus), with cycling parameters of denaturation at 94° C. for 1 min, primer annealing at 50° C. for 1.5 min, and primer extension at 72° C. for 2 min. As an internal standard, amplification of the actin mRNA was similarly done by reverse transcription-PCR by using the same RNA preparations and β-actin gene-specific sense (GCATGGAGTCCTGTGGCATCCACG, nucleotide positions 2563 to 2586) and anti-sense (CTAGAAGCATTTGCGGTGGACGAT, nucleotide positions 2977 to 3000) primers. A plasmid DNA containing the P protein gene of HPIV-3, kindly provided by Mark S. Galinski (The Cleveland Clinic Foundation, Cleveland, Ohio), was also used as a positive control in the PCR amplification. A PCR-amplified ~559 bp fragment from the P protein gene plasmid DNA was isolated by electrophoresis in a 0.8% agarose gel. The DNA band was excised, eluted by using an ultrafree MC column (Millipore Corporation, Bedford, Mass.), and radiolabeled with [$\alpha$-$^{32}$ P]dCTP by the random primed oligonucleotide labeling method by using a commercially available kit (Boehringer Mannheim Biochemicals, Indianapolis, Ind.), for use as a probe. An actin probe was similarly prepared for use in Southern hybridization.

mRNA synthesis was tested by comparing the levels of message between the two RNA preparations in a parallel experiment. The reaction products from different cycles PCR amplification were analyzed by agarose gel electrophoresis followed by ethidium bromide staining and showed a significant difference in the levels of message generated from cp45 and wild-type virus. On the other hand, similar message levels of the actin gene, studied as an internal control, was observed for the RNA isolated from cp45 and wild-type virus-infected cells. A similar observation was noted following Southern hybridization of the electrophoresed DNA. The typical amplification profile of the PCR products from viral mRNA is shown in FIG. 2(a). A semi-quantitative approach was taken for the estimation of the differences between these messages by slot blot hybridization with fourfold dilutions of a single cDNA sample. A representative example of the results, shown in FIG. 2(b), further indicates differences in the message of the P gene from cp45 and wild-type virus-infected cells at 15 and 20 cycles of PCR amplification. Message from the P protein gene of cp45 virus was estimated to be approximately 17% of that of wild-type virus by PhosphorImaging analysis.

Protein synthesis at the higher non-permissive temperature was also significantly lower in the cp45 strain as compared to the wild-type strain. cp45 virus polypeptide synthesis was analyzed by a pulse-chase experiment followed by immunoprecipitation with a hyperimmune rabbit antiserum to HPIV-3 or monoclonal antibodies to HN and NP.

Briefly, virus-infected cells were grown at 39.5° or 32° C. for 24 h and pulsed with $^{35}$S-protein label (Amersham Corporation, Arlington Heights, Ill.) for 1 h. Labeled cell lysates were immunoprecipitated after a chase of 0, 1, 2, 3, and 4 h with hyperimmune rabbit antiserum to HPIV-3 or with a pool of anti-HN and anti-NP monoclonal antibodies. Immunoprecipitates were analyzed by sodium dodecyl sulfate-polyacrylamide gel electrophoresis, followed by autoradiography.

Figure 3A:
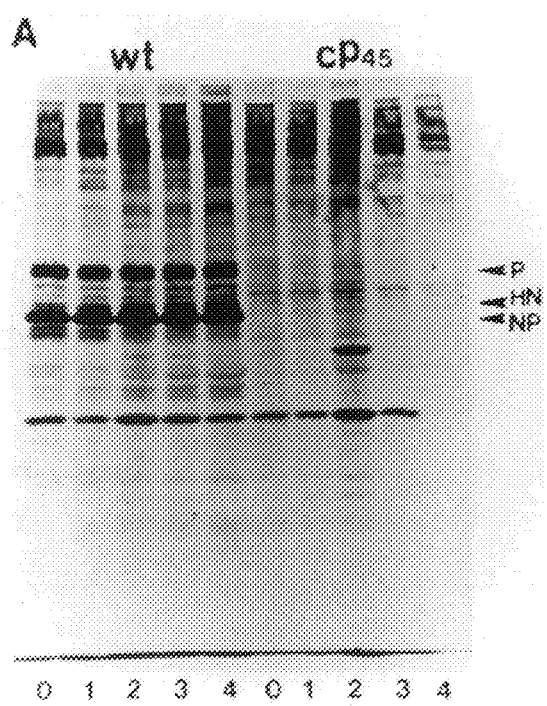
FIGS. 3(a) and 3(b) depict the results of a pulse-chase experiment, demonstrating the kinetics of viral protein synthesis.
Figure 3B:
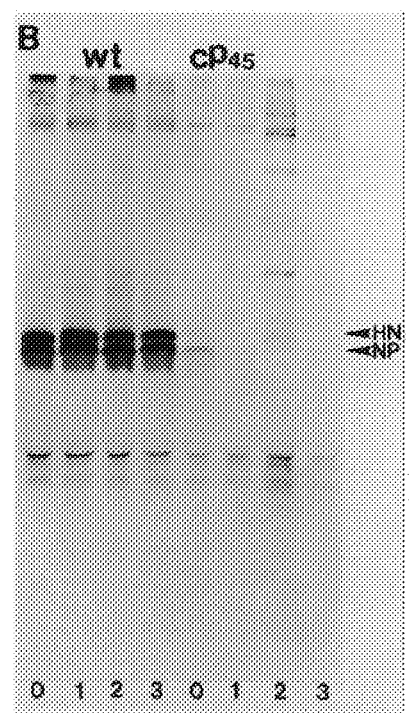

The results show a major difference in the synthesis of viral proteins between the wild-type and cp45 virus. Synthesis of wild-type virus polypeptides during the pulse period was not processed or modified further during the 4-h chase period (FIG. 3). On the other hand, cp45 virus polypeptide synthesis appeared to be extremely weak or almost undetectable. However, synthesis of cp45 and wild-type virus polypeptides was found to be similar when cells were grown at 32° C.

Example 2

Temperature-Dependent Neuraminidase Activity of cp45 cp45 virus was grown on L-132 cells at 32° or 39.5° C., and the virus-infected cell homogenate was analyzed for neuraminidase activities. The cp45 strain demonstrated a reduced neuraminidase activity of cp45 virus at the nonpermissive temperature higher temperature. Such a decrease in activity may inhibit the release of progeny virus particles from an infected cell surface.

Briefly, 100 $\mu$l of 0.2M sodium acetate buffer (pH 5.5) was mixed with an equal volume of infected cell homogenate with a known number of HA units. Then, 0.1 ml of bovine fetuin (15 mg/ml, type IV; Sigma Chemical Company, St. Louis, Mo.) dissolved in the same buffer was added to the reaction mixture, and the mixture was incubated at 37° C. overnight. The amount of released neuraminic acid in the reaction mixture was determined. Wild-type parent virus was also included in this study for comparison.

The neuraminidase property of the cp45 virus incubated at the nonpermissive temperature when tested with two different molecular-size substrates showed lower activity, by a factor ranging from about 4 to about 10, than cells infected with the wild-type virus (Table 2).

Example 3

Evaluation of Other Biological Properties of cp45

Antigenic relatedness of cp45 and the wild-type parent virus strain was initially compared by hemagglutination (HA) inhibition and neutralization assays using a monospecific rabbit antiserum to affinity-purified HPIV-3 HN glycoprotein. Rabbit anti-HN showed similar HA inhibition activities and neutralization titers (within twofold variation) with both the virus strains.

Subsequently, representative anti-HN and anti-F monoclonal antibodies recognizing distinct antigenic sites of the HN and F glycoprotein molecules were tested by enzyme-linked immunosorbent assay (ELISA). Dynatech polyvinyl plates (Immulon I) were coated with 1 $\mu$g of freeze-thaw disrupted virions per well. Monoclonal antibodies were tested at twofold serial dilutions for each virus strain (cp45 and the wild type), and the results were compared with the linear slopes of the reactivity pattern.

Figure 4A:
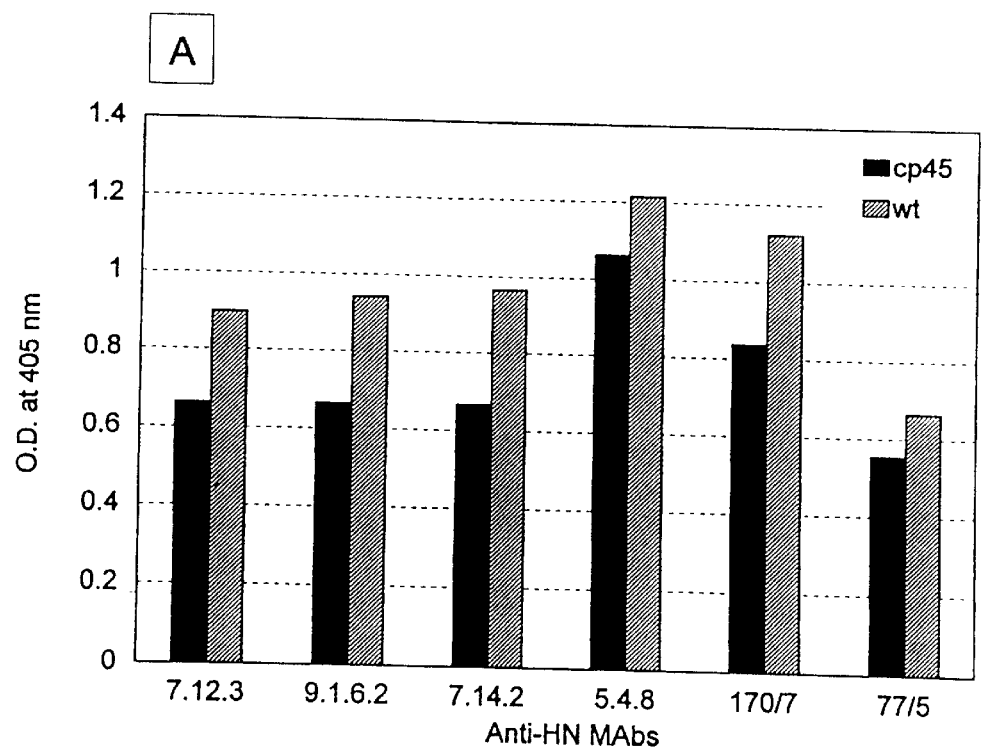
FIGS. 4(a) and 4(b) show the reactivities of cp45 and wild-type HPIV-3 with monoclonal antibodies to HN protein (FIG. 4(a)) and to F protein (FIG. 4(b)), as determined by ELISA.
Figure 4B:
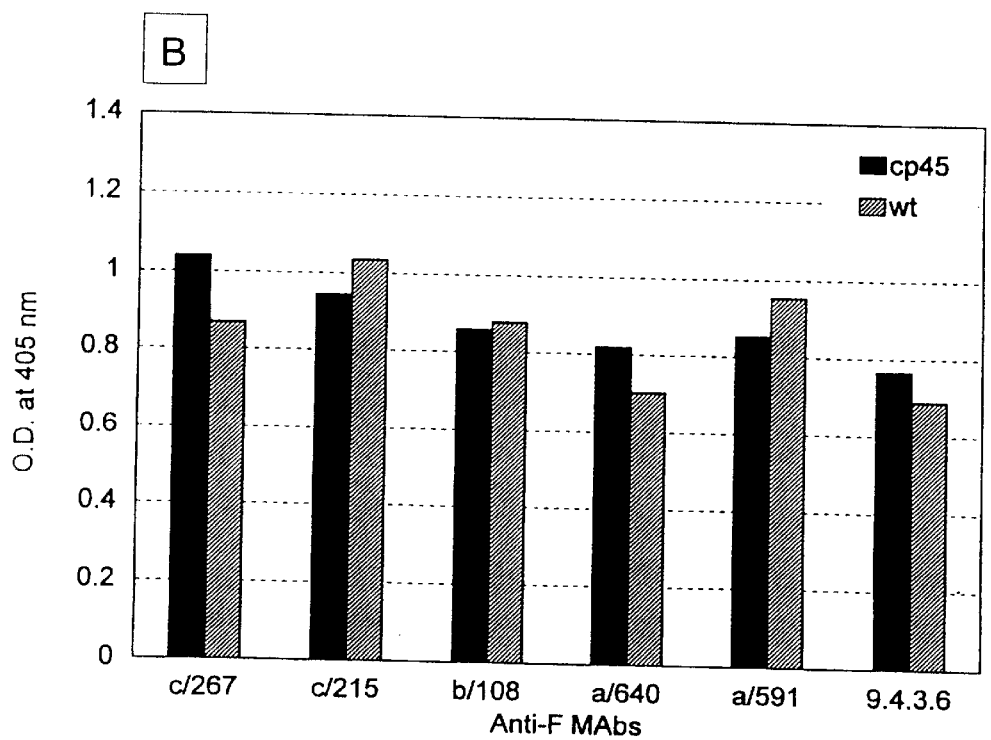

The results are presented (FIG. 4) as the mean optical densities from three independent experiments, showing variations within 0.05 to 0.08. The antibodies recognized the HN and F glycoproteins of cp45 virus and by ELISA showed a titers similar to that of the wild-type virus. This suggests that the antigenic sites of cp45 virus were not altered as a result of its adaptation for growth at 20° C.

Moreover, the cp45 virus glycoproteins are processed and transported to the cell surface even at the nonpermissive temperature. Infected L-132 cells were tested 24 h after infection by immunofluorescence with specific monoclonal antibodies to HN and F. Confluent monolayers of L-132 cells were grown on coverslips, infected with the virus, and incubated at 32° or 39.5° C. At 24 h postinfection, cells were washed with phosphate-buffered saline and tested with monoclonal antibodies. At both incubation temperatures (32° and 39.5° C.), cp45-infected cells showed immunofluorescence on the cell surface.

HA and fusion activity was also investigated. cp45 virus grown at 32° C. was pelleted by ultracentrifugation and used for an HA assay to test the functional property of the HN glycoprotein. As the cp45 virus showed extremely poor growth at 39.5° C., we tested the HA activity of infected cell homogenates following incubation at the nonpermissive temperature. Results showed detectable HA activity of the cp45 virus grown at the permissive or nonpermissive temperature. cp45 virus-infected LLC-MK$_2$, Vero, and L-132 cells also showed formation of multinucleated giant cells or syncytium formation, a characteristic of virus fusion activity, when grown at 32° C. However, fusion activity was significantly reduced upon incubation of cp45 virus-infected cells at 39.5° C., probably because of poor replication of the virus at the nonpermissive temperature.

Example 4

Expression of HPIV-3 NP, P and L Wild-Type Proteins

The molecular cloning and sequence analysis of the HPIV-3 NP, P, and L genes have been previously described. (Galinski et al. 1988; Galinski et al. 1986

1986'). Briefly, all genes were removed from their recombinant vectors by restriction endonuclease digestion and ligated into the appropriate sites of pcDL-SR beta 8.2 vector DNA. This vector is derived from pcDL-SR alpha-296 and contains a polyvalent restriction site with flanking T7 and SP6 promoter sequences downstream from the SR alpha promoter. pcDL-SR beta 8.2 is a multifunctional vector, and gene expression can be driven by using a simian virus 40 (SV40) early promoter or alternatively by using a vaccinia virus expressing T7 RNA polymerase.

Plasmids containing genomes which encode the NP, P and L proteins were incorporated into DNA vectors. Plasmid pSP18-NP, which contains the NP gene, was first digested with SphI, and the resulting cohesive end was repaired with T7 DNA polymerase. The gene was then released from the vector with BAMHI and ligated into pcDL-SR beta 8.2 which had been digested with EcoRI, subsequently repaired with Klenow fragment, and then further treated with BAMHI. Plasmid pSP19-P, which contains the P gene, was digested with BAMHI and PvuII to release the P gene. The gene was subsequently ligated into pcDL-SR beta 8.2 which had been digested with XbaI, subsequently repaired with Klenow fragment, and then further treated with BAMHI. Plasmid pGEM3-L, containing the L gene, was first digested with HindIII, and the resulting cohesive end was repaired with Klenow fragment. The L gene was then released from the vector with SacI and cloned into pcDL-SR beta 8.2 which has been digested with EcoRI, subsequently repaired with Klenow fragment, and then further treated with SacI.

All ligation reactions consisted of vector and gene fragments with compatible ends which would force ligation of the inserts in the desired orientation relative to the SR alpha and T7 promoters. Recombinant clones were randomly picked and further analyzed by restriction endonuclease digestion to confirm the orientation and efficacy of the subcloning. The gene termini were confirmed by dideoxy sequence analysis (U.S. Biochemical, Cleveland, Ohio) to ensure that the initiating methionine and termination codons were maintained.

To examine the biological properties of the various nucleocapsid-associated proteins, we initially tested for the protein expression of L (L-11), P (P-1), and NP (NP-1) in a transient expression system, using a recombinant vaccinia virus containing the bacteriophage T7 RNA polymerase gene (vTF7-3). HeLa-T4 cells, which are relatively resistant to the cytopathic effect of vaccinia virus, were infected with vTF7-3 and transfected with plasmids containing the HPIV-3 L, P, or NP gene, using Lipofectamine (Bethesda Research Laboratories, Gaithersburg, Md.).

Figure 5A:
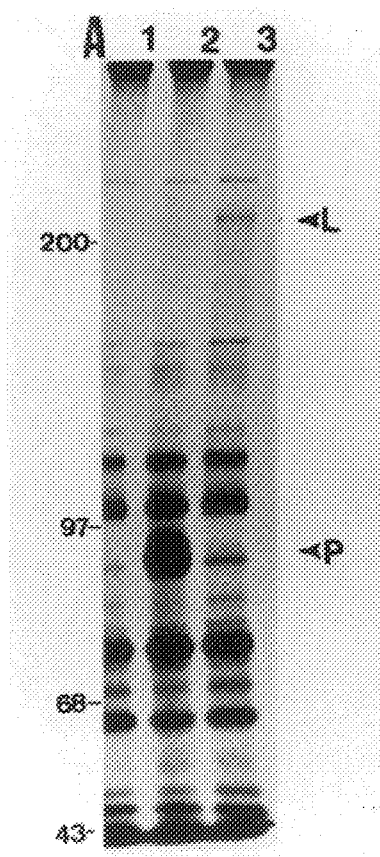
FIGS. 5(a) and 5(b) depict the immunoprecipitation of HPIV-3 proteins expressed by the vaccinia virus T7 system with rabbit antiserum (FIG. 5(a)) and with monoclonal antibodies (FIG. 5(b)).
Figure 5B:
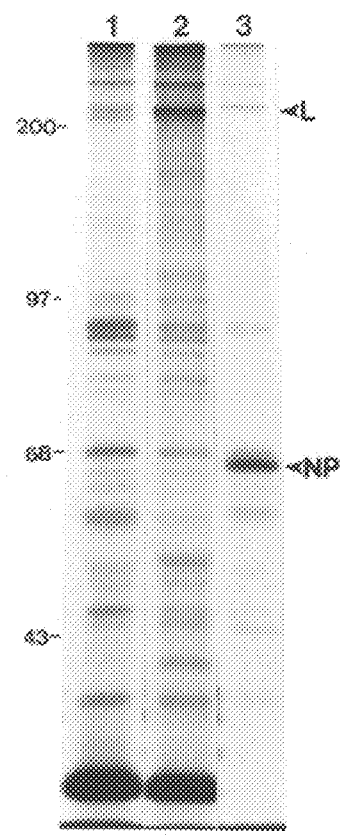
Figure 6A:
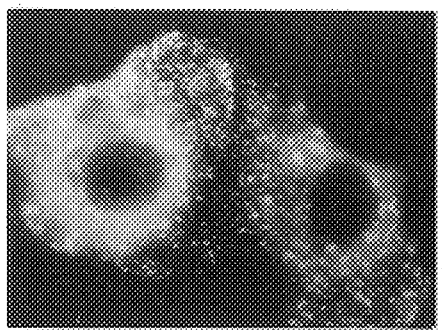
FIGS. 6(a) through 6(d) depict cells which have expressed HPIV-3 NP protein (FIG. 6(a)), P protein (FIG. 6(b)) or L protein (FIG. 6(c)), and shows their growth relative to a negative control (FIG. 4(d)).
Figure 6B:
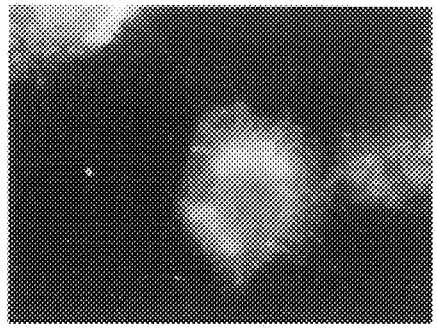
Figure 6C:
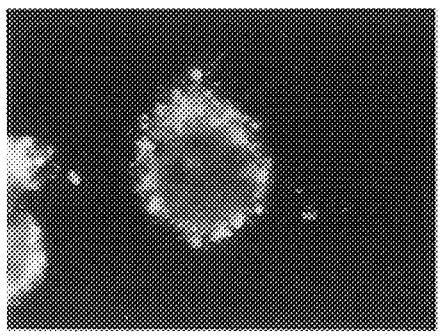
Figure 6D:
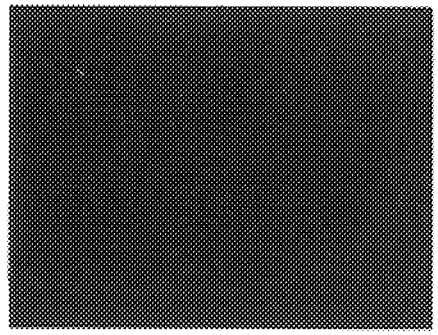

Expression of the viral L, P and NP proteins was detected after 20 h in [$^{35}$S]methionine-[$^{35}$S]cysteine-labeled transfected cell lysates by immunoprecipitation with a hyperimmune rabbit antiserum to HPIV-3 or a monoclonal antibody to NP (FIG. 5(a)). Immunoprecipitates were analyzed by sodium dodecyl sulfate (SDS)-polyacrylamide gel electrophoresis (PAGE) and autoradiography. To obtain better resolution of the large-molecular-size L protein, immunoprecipitates were also separated in a lower-percentage polyacrylamide gel (FIG. 5(b)). Immunoprecipitated L, P, and NP polypeptides from the corresponding DNA-transfected cells were indistinguishable in size from the authentic viral proteins. The amount of the L protein appeared to be lower than that of the P or NP protein immunoprecipitated by the antiserum from transfected cell lysates.

Example 5

Complementation of cp45 with Wild-Type Proteins

This example considers whether CV-1 cells which were transiently expressing the L, P or NP proteins could rescue (that is, increase the replication of the virus, as measured by plaque assay) cp45 at the nonpermissive temperature. Briefly, CV-1 cells were cotransfected with the plasmid vector pRSV-T (encoding the SV40 large T antigen driven by a Rous sarcoma virus long terminal repeat) and one or more recombinant plasmids containing the NP, P, or L gene and incubated at 37° C. Twenty hours posttransfection, the expressing cells were infected with cp45 or wild-type virus at a multiplicity of infection of 1, and infected cells were incubated for an additional 28 h at 39.5° C. Following incubation, cell culture medium was harvested and HPIV-3 titers were determined by plaque assay in L-132 cells at permissive (32° C.) and nonpermissive (39.5° C.) temperatures. Infected cell monolayers were stained with hematoxylin and eosin-Y or, alternatively, overlaid with 0.9% agar and 0.005% neutral red for visualization of viral plaques.

Although the vaccinia virus system provided excellent levels of expression, because of the concern regarding the use of a viral vector which causes extensive cytopathic effect in the cell monolayer and the difficulties inherent to measuring HPIV-3 replication in vaccinia virus coinfection experiments, we used an expression system which did not require the use of vaccinia virus to drive transcription of our plasmid vectors.

The vector pcDL-SR beta 8.2 contains a promoter, designated SR alpha, consisting of the SV40 early promoter and the R segment and part of the U5 sequence (R-U5') of the long terminal repeat of human T-cell leukemia virus type 1. The vector also contained the SV40 origin of replication and gives significant levels of protein expression in COS-1 or COS-7 cells, in which the plasmids are amplified by the endogenous levels of T antigen. The utility of this expression system was extended to CV-1 cells by coexpression in trans of the large T antigen from another plasmid vector, pRSV-T (35), kindly provided by James Pipas, University of Pittsburgh.

The transfected CV-1 cells were tested initially for intracellular expression of the viral proteins by immunofluorescence. Briefly, cells were fixed with acetone-methanol (1:1) for 10 min at −20° C. A hyperimmune rabbit antiserum to HPIV-3 (thoroughly preadsorbed with mock-transfected cells) was used as the primary antibody, and a fluorescein isothiocyanate tagged mouse anti-rabbit immunoglobulin G was used as the second antibody. Cells were examined at a magnification of 33 600 on a Nikon microscope equipped for epifluorescence, and digital photographs were captured by using a computer imaging system (Oncor Image Systems, Inc.).

As shown in FIG. 6, L and P appeared to form small inclusions, whereas NP seemed to give a more homogeneous, punctate staining pattern. Negative control cells did not show any detectable immunofluorescence.

The results of a typical complementation experiment are shown in Table 3; similar results were achieved in assays performed in triplicate. Virus yield at 39.5° C. showed significant levels of cp45 replication at the nonpermissive temperature. These results indicate that the wild-type L protein was biologically functional and could complement the temperature sensitive mutation of the cp45 L protein, whereas expression of P and NP in the absence of L was nonfunctional. The virus titer represents a complementation efficiency of approximately 950 and 11,500 PFU of virus per $3\times10^6$ cells. Cells transfected with L, P, and NP show a 10-fold increase in cp45 virus yield compared with cells transfected with L alone or with L and P. This may be due to interactions among these proteins for the formation of the nucleocapsid complex for efficient virus replication. However, their specific interactions during virus replication remain to be determined.

The results of this example further support the role of the L protein as an RNA-dependent RNA polymerase activity essential for transcription and the life cycle of HPIV-3. Other cell lines, not transfected with the L gene, failed to produce detectable virus titers.

Example 6

Ability of HPIV-1 L Protein to Complement cp45 and Retention of Temperature Sensitive Phenotype in cp45 Progeny cp45 virus produced from L-gene-transfected CV-1 cells at the nonpermissive temperature should remain temperature sensitive for growth despite their ability to replicate in L-expressing cells. At least 10 plaque-purified virus stocks of the progeny rescued virus were examined, and all virus stocks were found to have maintained their temperature sensitive property.

Further, L-protein complementation of cp45 is heterotypic exclusive. L-132 or primary rhesus monkey kidney cells, when coinfected with HPIV-1 and cp45, did not rescue growth of cp45 at the nonpermissive temperature.

Example 7 cp45-Hybrid Vaccines for HPIV-1, HPIV-2, RSV, Influenza-A, Influenza-B and Measles The methodology for producing cp45-hybrid vaccines is described above. Target viruses such as HPIV-1, HPIV-2, RSV, influenza and measles each have surface proteins which are functionally analogous to the F and HN proteins of HPIV-3. The nucleic acid sequences for each of these viruses is well known, as detailed below.

HPIV-1 and HPIV-2, like HPIV-3, each have two surface glycoproteins, HN and F, which are functionally similar to HPIV-3's HN and F proteins. For both type 1 and type 2 parainfluenza viruses, the H portion of the HN protein and the F protein are related to attachment and penetration, respectively, while the N portion of the HN protein is responsible for release of progeny virions. The nucleic acid sequences of the F gene and HN gene for HPIV-1 have been previously determined. (Merson et al. 1988; Matsuoka et al. 1990). The nucleic acid sequences of the F gene and the HN gene for HPIV-2 have likewise been determined. (Hu et al. 1990; Precious et al. 1990; Kawano et al. 1990'; Kawano et al. 1990)

RSV-A and RSV-B each have two surface glycoproteins, F and G. The G protein is functionally analogous to HPIV-3's HN protein; it has activities related to attachment onto a host cell, and following infection of the host, to release of progeny virions. F is related to penetration of the nucleocapsid into the host cell. The nucleic acid sequences of the F gene and G gene for RSV-A have been determined. (Lopez et al. 1988; Martin-Gallardo et al. 1991; Anderson et al. 1992; Martin-Gallardo et al. 1993; Collins et al. 1993). The nucleic acid sequences of the F gene and G gene for RSV-B have also been previously determined. (Baybutt and Pringle 1987; Sullender et al. 1990; Sullender et al. 1991). These sequences or portions thereof have also been extensively compared. (Johnson and Collins 1988; Johnson and Collins 1988').

Influenza types A and B also have two surface glycoproteins: H and N. The H protein has activities related to attachment and penetration onto and into a host cell. The N protein relates to release of progeny virions from the infected host. Although the antigenic sites for influenza viruses typically change every year or so, samples of current strains are readily available from the U.S. Center for Infectious Disease Control, and the nucleic acid sequences defining the current surface glycoproteins can be determined therefrom.

Measles viruses also has two surface glycoproteins: HN and F. Like HPIV-3, the H portion of the HN protein and the F protein are related to attachment and penetration, respectively, while the N portion of the HN protein is responsible for release of progeny virions.

Bovine RSV has two surface glycoproteins which are functionally analogous to the human RSV strains. The nucleic acid sequences for bovine RSV G and F glycoproteins have been determined. (Lerch et al. 1990; Walravens et al. 1990).

In light of the detailed description of the invention and the examples presented above, it can be appreciated that the several objects of the invention are achieved.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention.

BIBLIOGRAPHY

Anderson, et al. 1992. Intracellular processing of the human respiratory syncytial virus fusion glycoprotein: Amino acid substitutions affecting folding, transport and cleavage. J. Gen. Virol. 73(Pt. 5):1177–88.

Belshe and Hissom 1982. Cold adaptation of parainfluenza virus type induction of three phenotypic markers. J. Med. Virol. 10:235–242.

Belshe, et al. 1992. Evaluation of a live attenuated, cold-adapted parainfluenza virus type 3 vaccine in children. J. Clin. Microbiol. 30:2064–2070.

Baybutt and Pringle 1987. Molecular cloning and sequencing of the F and 22K membrane protein genes of the RSS-2 strain of respiratory syncytial virus. J. Gen. Virol. 68 (Pt 11):2789–96.

Clements, et al. 1991. Evaluation of bovine, cold-adapted human, and wild-type human parainfluenza type 3 viruses in adult volunteers and in chimpanzees. J. Clin. Microbiol. 29:1175–1182.

Collins, et al. 1993. Rescue of a 7502-nucleotide (49.3% of full-length) synthetic analog of respiratory syncytial virus genomic RNA. Virol. 195(1):252–6.

Crookshanks-Newman and Belshe. 1986. Protection of weanling hamsters from experimental infection with wild-type parainfluenza virus type 3 (para 3) by cold-adapted mutants of para 3.J. Med. Virol. 18:131–137.

Galinski et al. 1986. Molecular cloning and sequence analysis of the human parainfluenza 3 virus RNA encoding the nucleocapsid protein. Virol. 149:139–151.

Galinski et al. 1986'. Molecular cloning and sequence analysis of the human parainfuenza 3 virus mRNA encoding the P and C proteins. Virol. 154:46–60.

Galinski et al. 1988. Molecular cloning and sequence analysis of the human parainfluenza 3 virus gene encoding the L protein. Virol. 165:499–510.

Hall et al. 1993. A cold-adapted mutant of parainfluenza virus type 3 is attenuated and protective in chimpanzees. J. Infect. Dis. 167:958–962.

Hu, et al. 1990. Molecular cloning and sequence analysis of the fusion glycoprotein gene of human parainfluenza virus type 2. Virol. 179(2):915–20.

Johnson and Collins 1988. The A and B subgroups of human respiratory syncytial virus: Comparison of intergenic and gene-overlap sequences. J. Gen. Virol. 69(Pt 11):2901–6.

Johnson and Collins 1988'. The fusion glycoproteins of human respiratory syncytial virus of subgroups A and B: Sequence conservation provides a structural basis for antigenic relatedness. J. Gen. Virol. 69(Pt 10):2623–8.

Karron et al. 1995. A Live Human Parainfluenza Type 3 Virus Vaccine is Attenuated and Immunogenic in Healthy Infants and Children. The Journal of Infectious Diseases 172:1445–1450.

Kawano, et al. 1990. Sequence determination of the hemagglutinin-neuraminidase (HN) gene of human parainfluenza type 2 virus and the construction of a phylogenetic tree for HN proteins of all the paramyxoviruses that are infectious to humans. Virol. 174(1):303–13.

Kawano, et al. 1990'. Sequence of the fusion protein gene of human parainfluenza type 2 virus and its 3' intergenic region: Lack of small hydrophobic (SH) gene. Virol. 178(1):289–92.

Kuppuswamy, et al. 1991. Single nucleotide primer extension to detect genetic diseases: Experimental application to hemophilia B (factor IX) and cystic fibrosis genes. Proc. Natl. Acad. Sci. USA. 88:1143–1147.

Lawson et al. 1995. Recombinant vesicular stomatitis viruses from DNA. Proc. Natl. Acad. Sci. USA 92:4477–4481.

Lerch, et al. 1990. Nucleotide sequence analysis and expression from recombinant vectors demonstrates that the attachment protein G of bovine respiratory syncytial virus is distinct from that of human respiratory syncytial virus. J. Virol. 64(11):5559–69.

Lopez, et al. 1988. Nucleotide sequence of the fusion and phosphoprotein genes of human respiratory syncytial (RS) virus long strain: Evidence of subtype genetic heterogeneity. Virus Research. 10(2–3):249–61.

Martin-Gallardo, et al. 1991. Expression of the F glycoprotein gene from human respiratory syncytial virus in Escherichia coli: Mapping of a fusion inhibiting epitope. Virol. 184(1):428–32.

Martin-Gallardo, et al. 1993. Expression of the G glycoprotein gene of human respiratory syncytial virus in Salmonella typhimurium. J. Gen. Virol. 74(Pt.3):453–8.

Matsuoka, et al. 1990. Sequence of the hemagglutinin-neuraminidase gene of human parainfluenza virus type 1. Virus Research. 16(1):107–13.

Merson, et al. 1988. Molecular cloning and sequence determination of the fusion protein gene of human parainfluenza virus type 1. Virol. 167(1):97–105.

Palese, P. 1995. Genetic engineering of infectious negative-strand RNA viruses. [Review]. Trends in Microbiology. 3(4):123–5.

Precious, et al. 1990. Sequence analysis of the HN gene of parainfluenza virus type 2. J. Gen. Virol. 71(Pt 5):1163–8.

Schnell et al. 1994. Infectious rabies viruses from clone cDNA. EMBO J. 13:4195–4203.

Spriggs and Collins 1986. Human parainfluenza virus type 3: messenger RNAs, polypeptide coding assignments, intergenic sequences, and genetic map. J. Virol. 59:646–654.

Spriggs and Collins 1986'. Sequence analysis of the P and C protein genes of human parainfluenza virus type 3: Patterns of amino acid sequence homology among paramyxovirus proteins. J. Gen. Virol. 67:2705–2719.

Stokes, et al. 1993. The complete nucleotide sequence of two-cold adapted, temperature-sensitive attenuated mutant vaccine viruses (cp12 and cp45) derived from the JS strain of human parainfluenza virus type 3 (PIV3). Virus Res. 30:43–52.

Storey, et al. 1984. Structural characterization of viron proteins and genomic RNA of human parainfluenza virus 3. J. Virol. 52:761–766.

Sullender, et al. 1990. The respiratory syncytial virus subgroup B attachment glycoprotein: Analysis of sequence, expression from a recombinant vector, and evaluation as an immunogen against homologous and heterologous subgroup virus challenge. Virol. 178(1):195–203.

Sullender, et al. 1991. Genetic diversity of the attachment protein of subgroup B respiratory syncytial viruses. J. Virol. 65(10):5425–34.

Walravens, et al. 1990. Sequence comparison between the fusion protein of human and bovine respiratory syncytial viruses. J. Gen. Virol. 71 (Pt 12):3009–14.

---

What is claimed is:

1. A hybrid virus comprising
an enveloped, negative-sense, single-stranded RNA virus, the virus having a genome which includes (i) a nucleic acid sequence which encodes each surface antigen of an enveloped, negative-sense, single-stranded RNA target virus selected from the group consisting of HPIV-1, HPIV-2 and RSV, and (ii) a nucleic acid sequence which encodes a variant HPIV-3 large protein, L, the variant L protein having polymerase activity and having at least two substitutions in amino acid sequence relative to the L protein of wild-type HPIV-3 (JS), the substitutions being His for Tyr at residue 942 of SEQ ID NO:1 and Phe for Leu at residue 992 of SEQ ID NO:1, the variant L protein attenuating replication of the virus relative to the target virus by a factor of at least about 10 as determined by virus-yield assay at 39° C.

2. The vaccine of claim 1 wherein the genome of the virus further comprises: (i) a nucleic acid sequence which encodes the nucleocapsid protein, (NP), of a HPIV-3 virus and (ii) a nucleic acid sequence which encodes the phosphoprotein, P(+C), of a HPIV-3 virus.

3. The vaccine of claim 1 wherein the genome of the virus further comprises: (i) a nucleic acid sequence which is the same as the nucleic acid sequence of the 3' leader region of a HPIV-3 viral genome; (ii) a nucleic acid sequence which encodes the nucleocapsid protein, (NP), of a HPIV-3 virus; (iii) a nucleic acid sequence which encodes the phosphoprotein, P(+C), of a HPIV-3 virus; and (iv) a nucleic acid sequence which encodes the matrix protein, (M), of a HPIV-3 virus.

4. A live, attenuated vaccine comprising
an enveloped, negative-sense, single-stranded RNA virus, the virus having a genome which comprises: (i) a nucleic acid sequence which is the same as the nucleic acid sequence of the 3' leader region of a human parainfluenza virus (HPIV) type 3 viral genome; (ii) a nucleic acid sequence which encodes the nucleocapsid protein, (NP), of a HPIV-3 virus; (iii) a nucleic acid sequence which encodes the phosphoprotein, P(+C), of a HPIV-3 virus; (iv) a nucleic acid sequence which encodes the matrix protein, (M), of a HPIV-3 virus; (v) a nucleic acid sequence which encodes each surface antigen of an enveloped, negative-sense, single-stranded RNA target virus selected from the group consisting of HPIV-1, HPIV-2, and respiratory syncytial virus (RSV); and (vi) a nucleic acid sequence which encodes a variant HPIV-3 large protein, (L), the variant L protein having polymerase activity and having at least two substitutions in amino acid sequence relative to the L protein of wild-type HPIV-3 (JS), the substitutions being His for Tyr at residue 942 of SEQ ID NO: 1 and Phe for Leu at residue 992 of SEQ ID NO: 1, the variant L protein attenuating replication of the virus relative to the target virus by a factor of at least about 10 as determined by virus-yield assay at 39° C., and a pharmaceutically appropriate carrier.

5. The vaccine of claim 4 wherein the substitutions in amino acid sequence of the variant L protein further comprise the substitution of Ile for Thr at residue 1558 of SEQ ID NO:1.

6. The vaccine of claim 4 wherein the variant L protein is the cp45 L protein.

7. The vaccine of claim 4 wherein the variant L protein is an RNA-dependent RNA polymerase having polymerase activity which is at least about 10 times less than the polymerase activity of the target virus at a temperature of about 39° C.

8. The vaccine of claim 4 wherein the variant L protein is associated with a temperature sensitive phenotype of the vaccine.

9. The vaccine of claim 4 wherein the 3' leader region of the HPIV-3 genome is the 3' leader region of the cp45 genome.

10. The vaccine of claim 4 wherein the HPIV-3 phosphoprotein is the phosphoprotein of cp45.

11. The vaccine of claim 4 wherein the HPIV-3 matrix protein is the matrix protein of cp45.

12. The vaccine of claim 4 wherein the 3' leader region of the HPIV-3 genome is the 3' leader region of the cp45 genome and the HPIV-3 NP, P(+C), and M proteins are cp45 NP, P(+C) and M proteins.

13. The vaccine as set forth in claim 4 wherein the target virus is a HPIV-1 virus.

14. The vaccine as set forth in claim 4 wherein the target virus is a HPIV-2 virus.

15. The vaccine as set forth in claim 4 wherein the target virus is a RSV virus.

16. The vaccine as set forth in claim 4 wherein the RSV target virus is an non-animal animal virus.

17. A live, attenuated human vaccine comprising
an enveloped, negative-sense, single-stranded RNA virus, the virus having a genome which comprises, in succession from its 3' end: (i) a nucleic acid sequence which is the same as the nucleic acid sequence of the 3' leader region of the cp45 viral genome; (ii) a nucleic acid sequence which encodes the nucleocapsid protein, (NP), of cp45; (iii) a nucleic acid sequence which encodes the phosphoprotein, P(+C), of cp45; (iv) a nucleic acid sequence which encodes the matrix protein, (M), of cp45; (v) a nucleic acid sequence which encodes both surface antigens of a target virus selected from the group consisting of HPIV-1, HPIV-2 and RSV; and (vi) a nucleic acid sequence which encodes a variant HPIV-3 large protein, L, the variant L protein having polymerase activity and having at least two substitutions in amino acid sequence relative to the wild-type HPIV-3 (JS) L protein, the substitutions being His for Tyr at residue 942 of SEQ ID NO:1 and Phe for Leu at residue 992 of SEQ ID NO:1; the variant L protein attenuating replication of the virus relative to the target virus by a factor of at least about 10 as determined by virus-yield assay at 39° C.; and a pharmaceutically appropriate carrier.

18. The vaccine as set forth in claim 17 wherein the substitutions in amino acid sequence of the variant L protein relative to the further comprise the substitution of Phe for Leu at residue 992 of SEQ ID NO:1 and Ile for Thr at residue 1558 of SEQ ID NO:1.

19. The vaccine as set forth in claim 17 wherein the variant L protein is the cp45 L protein.

20. The vaccine as set forth in claim 17 wherein the viral genome further comprises non-coding intergenic regions.

21. The vaccine as set forth in claim 17 wherein the target virus is a HPIV-1 virus.

22. The vaccine as set forth in claim 17 wherein the target virus is a HPIV-2 virus.

23. The vaccine as set forth in claim 17 wherein the target virus is a RSV virus.

24. A hybrid virus comprising an enveloped, negative-sense, single-stranded chimeric RNA genome, the genome including, in succession from its 3' end:

(i) a nucleic acid sequence which is the same as the nucleic acid sequence of the 3' leader region of cp45 viral genome;

(ii) a nucleic acid sequence which encodes the nucleocapsid protein, (NP), of cp45;

(iii) a nucleic acid sequence which encodes the phosphoprotein, P(+C), of cp45;

(iv) a nucleic acid sequence which encodes the matrix protein, (M), of cp45;

(v) a nucleic acid sequence which encodes each surface antigen of an enveloped, negative-sense, single-stranded RNA target virus selected from the group consisting of HPIV-1, HPIV-2 and RSV; and (vi) a nucleic acid sequence which encodes a variant HPIV-3 large protein, L, the variant L protein having polymerase activity and having at least two substitutions in amino acid sequence relative to the L protein of wild-type HPIV-3 (JS), the substitutions being His for Tyr at residue 942 of SEQ ID NO:1 and Phe for Leu at residue 992 of SEQ ID NO:1, the variant L protein attenuating replication of the virus relative to the target virus by a factor of at least about 10 as determined by virus-yield assay at 39° C.

25. The virus as set forth in claim 24 wherein the substitutions in amino acid sequence of the variant L protein further comprise the substitution of Ile for Thr at residue 1558 of SEQ ID NO:1.

26. The hybrid virus of claim 24 wherein the variant L protein is associated with a temperature sensitive phenotype of the vaccine.

27. The hybrid virus as set forth in claim 24 wherein the RSV target virus is an non-human animal virus.

28. The hybrid virus as set forth in claim 24 wherein the variant L protein is the cp45 L protein.

29. The hybrid virus of claim 24 wherein the target virus is a HPIV-1 virus.

30. The hybrid virus of claim 24 wherein the target virus is a HPIV-2 virus.

31. The hybrid virus of claim 24 wherein the target virus is a RSV virus.

32. A hybrid virus comprising an enveloped, negative-sense, single-stranded chimeric RNA genome, the genome including, in succession from its 3' end: (i) a nucleic acid sequence which is the same as the nucleic acid sequence of the 3' leader region of cp45 viral genome; (ii) a nucleic acid sequence which encodes the nucleocapsid protein, (NP), of cp45; (iii) a nucleic acid sequence which encodes the phosphoprotein, P(+C), of cp45; (iv) a nucleic acid sequence which encodes the matrix protein, (M), of cp45; (v) a nucleic acid sequence which encodes each surface antigen of an enveloped, negative-sense, single-stranded RNA target virus selected from the group consisting of HPIV-1, HPIV-2 and RSV; and (vi) a nucleic acid sequence which encodes the large protein, L, of cp45.

33. The hybrid virus of claim 32 wherein the target virus is a HPIV-1 virus.

34. The hybrid virus of claim 32 wherein the target virus is a HPIV-2 virus.

35. The hybrid virus of claim 32 wherein the target virus is a RSV virus.

36. The hybrid virus of claim 32 wherein the RSV target virus is an non-human animal virus.

37. A method for producing an enveloped, negative-sense, single-stranded RNA virus, the method comprising:

transfecting a mammalian host cell with a vector, the vector comprising a chimeric genome, the genome including (i) a nucleic acid sequence which encodes each surface antigen of an enveloped, negative-sense, single-stranded RNA target virus selected from the group consisting of HPIV-1, HPIV-2 and RSV, and (ii) a nucleic acid sequence which encodes a variant HPIV-3 large protein, L, the variant L protein having at least two substitutions in amino acid sequence relative to the L protein of wild-type HPIV-3 (JS), the substitutions being His for Tyr at residue 942 of SEQ ID NO:1 and Phe for Leu at residue 992 of SEQ ID NO:1, and having an RNA polymerase activity which is at least about 10 times less than the polymerase activity of the target virus at a temperature of about 39° C.;

cotransfecting the host cell with vectors that express HPIV-3 NP, P and L proteins;

incubating the transfected host cell to produce a hybrid virus; and isolating the hybrid virus.

38. The method as set forth in claim 37 wherein the substitutions in amino acid sequence of the variant L protein further comprise the substitution of Ile for Thr at residue 1558 of SEQ ID NO:1.

39. The method as set forth in claim 37 wherein the genome further includes: (i) a nucleic acid sequence which is the same as the nucleic acid sequence of the 3' leader region of a cp45 viral genome, (ii) a nucleic acid sequence which encodes the nucleocapsid protein, (NP), of cp45, (iii) a nucleic acid sequence which encodes the phosphoprotein, P(+C), of cp45, (iv) a nucleic acid sequence which encodes the matrix protein, (M), of cp45.

40. The method as set forth in claim 37 wherein the genome is a positive-sense or negative-sense genome.

41. A plasmid vector comprising a chimeric RNA genome which includes (i) a nucleic acid sequence which encodes each surface antigen of an enveloped, negative-sense, single-strand RNA target virus selected from the group consisting of HPIV-1, HPIV-2 and RSV, and (ii) a nucleic acid sequence which encodes a HPIV-3 large protein, L, the variant L protein having at least two substitutions in amino acid sequence relative to the L protein of wild-type HPIV-3 (JS), the substitutions being His for Tyr at residue 942 of SEQ ID NO:1 and Phe for Leu at residue 992 of SEQ ID NO:1, and having an RNA polymerase activity which is at least about 10% less than the polymerase activity of the target virus at a temperature of about 39° C., the sense of the genome being either positive or negative.

42. A host cell transfected with the plasmid vector set forth in claim 41.

43. A method for determining whether an enveloped, negative-sense, single-stranded RNA virus having a genome which encodes a HPIV-3 large protein, L is attenuated, the method comprising confirming the presence of at least one variation in the genome of the virus relative to the genome of wild-type HPIV-3 (JS), the variations being in the region of the genome which encodes the L protein and effecting at least one substitution in the L-Protein of the virus relative to the L-protein of wild-type HPIV-3(JS), the substitution being selected from the group consisting of His for Tyr at residue 942 of SEQ ID NO:1, and Phe for Leu at residue 992 of SEQ ID NO:1 and Ile for Thr at residue 1558 of SEQ ID NO:1.

44. The method of claim 43 wherein the virus is a HPIV-3 virus.

45. The method of claim 43 wherein the virus is a progeny virus of an enveloped, negative-sense, single-stranded RNA parent virus, the parent virus having a genome which comprises, in succession from its 3' end: (i) a nucleic acid sequence which is the same as the nucleic acid sequence of the 3' leader region of the cp45 viral genome; (ii) a nucleic acid sequence which encodes the nucleocapsid protein, (NP), of cp45; (iii) a nucleic acid sequence which encodes the phosphoprotein, P(+C), of cp45; (iv) a nucleic acid sequence which encodes the matrix protein, (M), of cp45; (v) a nucleic acid sequence which encodes each surface antigen of an enveloped target virus, each surface antigen being different from the surface antigens of cp45 and (vi) a nucleic acid sequence which encodes a variant HPIV-3 large protein, L, the variant L protein having polymerase activity and having at least two substitutions in amino acid sequence relative to the wild-type HPIV-3 (JS) L protein, the substitutions being His for Tyr at residue 942 of SEC ID NO:1 and Phe for Leu at residue 992 of SEQ ID NO: 1, the variant L protein attenuating replication of the parent virus relative to the target virus by a factor of at least about 10 as determined by virus-yield assay at 39° C.

46. The method of claim 43 wherein at least two substitutions are effected in the L-protein of the virus relative to the L-protein of wild-type HPIV-3(JS), the substitutions being His for Tyr at residue 942 of SEQ ID NO:1 and Phe for Leu at residue 992 of SEQ ID NO:1.

47. The method of claim 43 wherein the substitutions effected in the L-protein of the virus relative to the L-protein of wild-type HPIV-3(JS) include His for Tyr at residue 942 of SEQ ID NO:1, Phe for Leu at residue 992 of SEQ ID NO:1, and Ile for Thr at residue 1558 of SEQ ID NO:1.

48. The method of claim 43 wherein the virus is cp45.

49. A method for determining whether an enveloped, negative-sense, single-stranded RNA virus having a genome which encodes a HPIV-3 large protein, L, is attenuated, the method comprising obtaining a sample of the virus to be tested;

performing a first plaque assay on the sample to determine the number of virus present in the sample;

transfecting a mammalian host cell in vitro with a plasmid vector that expresses L protein of a wild-type HPIV-3 virus;

infecting the host cell with the virus being tested;

incubating to yield a complemented virus;

performing a second plaque assay on a sample of the complemented virus to determine the number of virus present in the complemented sample; and comparing the second plaque assay to the first plaque assay to determine whether the virus is attenuated.

50. The method of claim 49 further comprising cotransfecting the host cell with a plasmid vector that expresses P protein of wild-type HPIV-3.

51. The method of claim 49 further comprising cotransfecting the host cell with a plasmid vector that expresses NP protein of wild-type HPIV-3.

52. The method of claim 49 wherein the virus is a HPIV-3 virus.

53. The method of claim 49 wherein the virus is a progeny virus of an enveloped, negative-sense, single-stranded RNA parent virus, the parent virus having a genome which comprises, in succession from its 3' end: (i) a nucleic acid sequence which is the same as the nucleic acid sequence of the 3' leader region of the cp45 viral genome; (ii) a nucleic acid sequence which encodes the nucleocapsid protein, (NP), of cp45; (iii) a nucleic acid sequence which encodes the phosphoprotein, P(+C), of cp45; (iv) a nucleic acid sequence which encodes the matrix protein, (M), of cp45; (v) a nucleic acid sequence which encodes each surface antigen of an enveloped target virus, each surface antigen being different from the surface antigens of cp45 and (vi) a nucleic acid sequence which encodes a variant HPIV-3 large protein, L, the variant L protein having polymerase activity and having at least two substitutions in amino acid sequence relative to the wild-type HPIV-3 (JS) L protein, the substitutions being His for Tyr at residue 942 of SEQ ID NO:1 and Phe for Leu at residue 992 of SEQ ID NO: 1, the variant L protein attenuating replication of the parent virus relative to the target virus by a factor of at least about 10 as determined by virus-yield assay at 39° C.

54. The method of claim 49 wherein the virus is cp45.

55. The virus of claim 1 wherein the variant L protein is the cp45 L protein.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 2233 amino acids
        ( B ) TYPE: amino acid
        ( C ) STRANDEDNESS: single
        ( D ) TOPOLOGY: linear ( i i ) MOLECULE TYPE: protein ( v i ) ORIGINAL SOURCE:
        ( A ) ORGANISM: Human parainfluenza virus 3
        ( B ) STRAIN: JS ( x i ) SEQUENCE DESCRIPTION: SEQ ID NO:1:

Met  Asp  Thr  Glu  Ser  Asn  Asn  Gly  Thr  Val  Ser  Asp  Ile  Leu  Tyr  Pro

-continued

|     | 1   |     |     |     | 5   |     |     |     |     | 10  |     |     |     |     | 15  |
|-----|-----|-----|-----|-----|-----|-----|-----|-----|-----|-----|-----|-----|-----|-----|-----|
|     | Glu | Cys | His | Leu | Asn | Ser | Pro | Ile | Val | Lys | Gly | Lys | Ile | Ala | Gln | Leu |
|     |     |     |     | 20  |     |     |     |     | 25  |     |     |     | 30  |     |     |
|     | His | Thr | Ile | Met | Ser | Leu | Pro | Gln | Pro | Tyr | Asp | Met | Asp | Asp | Ser |
|     |     |     | 35  |     |     |     | 40  |     |     |     | 45  |     |     |     |     |
|     | Ile | Leu | Val | Ile | Thr | Arg | Gln | Lys | Ile | Lys | Leu | Asn | Lys | Leu | Asp | Lys |
|     |     | 50  |     |     |     | 55  |     |     |     | 60  |     |     |     |     |     |
|     | Arg | Gln | Arg | Ser | Ile | Arg | Arg | Leu | Lys | Leu | Ile | Leu | Thr | Glu | Lys | Val |
|     | 65  |     |     |     | 70  |     |     |     | 75  |     |     |     |     | 80  |     |
|     | Asn | Asp | Leu | Gly | Lys | Tyr | Thr | Phe | Ile | Arg | Tyr | Pro | Glu | Met | Ser | Lys |
|     |     |     |     | 85  |     |     |     | 90  |     |     |     |     | 95  |     |     |
|     | Glu | Met | Phe | Lys | Leu | Tyr | Ile | Pro | Gly | Ile | Asn | Ser | Lys | Val | Thr | Glu |
|     |     |     |     | 100 |     |     |     | 105 |     |     |     | 110 |     |     |     |
|     | Leu | Leu | Leu | Lys | Ala | Asp | Arg | Thr | Tyr | Ser | Gln | Met | Thr | Asp | Gly | Leu |
|     |     |     | 115 |     |     |     | 120 |     |     |     | 125 |     |     |     |     |
|     | Arg | Asp | Leu | Trp | Ile | Asn | Val | Leu | Ser | Lys | Leu | Ala | Ser | Lys | Asn | Asp |
|     |     | 130 |     |     |     | 135 |     |     |     | 140 |     |     |     |     |     |
|     | Gly | Ser | Asn | Tyr | Asp | Leu | Asn | Glu | Glu | Ile | Asn | Asn | Ile | Ser | Lys | Val |
|     | 145 |     |     |     | 150 |     |     |     | 155 |     |     |     |     | 160 |     |
|     | His | Thr | Thr | Tyr | Lys | Ser | Asp | Lys | Trp | Tyr | Asn | Pro | Phe | Lys | Thr | Trp |
|     |     |     |     | 165 |     |     |     | 170 |     |     |     | 175 |     |     |     |
|     | Phe | Thr | Ile | Lys | Tyr | Asp | Met | Arg | Arg | Leu | Gln | Lys | Ala | Arg | Asn | Glu |
|     |     |     |     | 180 |     |     |     | 185 |     |     |     | 190 |     |     |     |
|     | Ile | Thr | Phe | Asn | Val | Gly | Lys | Asp | Tyr | Asn | Leu | Leu | Glu | Asp | Gln | Lys |
|     |     |     | 195 |     |     |     | 200 |     |     |     | 205 |     |     |     |     |
|     | Asn | Phe | Leu | Leu | Ile | His | Pro | Glu | Leu | Val | Leu | Ile | Leu | Asp | Lys | Gln |
|     |     | 210 |     |     |     | 215 |     |     |     | 220 |     |     |     |     |     |
|     | Asn | Tyr | Asn | Gly | Tyr | Leu | Ile | Thr | Pro | Glu | Leu | Val | Leu | Met | Tyr | Cys |
|     | 225 |     |     |     | 230 |     |     |     | 235 |     |     |     |     | 240 |     |
|     | Asp | Val | Val | Glu | Gly | Arg | Trp | Asn | Ile | Ser | Ala | Cys | Ala | Lys | Leu | Asp |
|     |     |     |     | 245 |     |     |     | 250 |     |     |     | 255 |     |     |     |
|     | Pro | Lys | Leu | Gln | Ser | Met | Tyr | Gln | Lys | Gly | Asn | Asn | Leu | Trp | Glu | Val |
|     |     |     |     | 260 |     |     |     | 265 |     |     |     | 270 |     |     |     |
|     | Ile | Asp | Lys | Leu | Phe | Pro | Ile | Met | Gly | Glu | Lys | Thr | Phe | Asp | Val | Ile |
|     |     |     | 275 |     |     |     | 280 |     |     |     | 285 |     |     |     |     |
|     | Ser | Leu | Leu | Glu | Pro | Leu | Ala | Leu | Ser | Leu | Ile | Gln | Thr | His | Asp | Pro |
|     |     | 290 |     |     |     | 295 |     |     |     | 300 |     |     |     |     |     |
|     | Val | Lys | Gln | Leu | Arg | Gly | Ala | Phe | Leu | Asn | His | Val | Leu | Ser | Glu | Met |
|     | 305 |     |     |     | 310 |     |     |     | 315 |     |     |     |     | 320 |     |
|     | Glu | Leu | Ile | Phe | Glu | Ser | Arg | Glu | Ser | Ile | Lys | Glu | Phe | Leu | Ser | Val |
|     |     |     |     | 325 |     |     |     | 330 |     |     |     | 335 |     |     |     |
|     | Asp | Tyr | Ile | Asp | Lys | Ile | Leu | Asp | Ile | Phe | Asn | Lys | Ser | Thr | Ile | Asp |
|     |     |     |     | 340 |     |     |     | 345 |     |     |     | 350 |     |     |     |
|     | Glu | Ile | Ala | Glu | Ile | Phe | Ser | Phe | Phe | Arg | Thr | Phe | Gly | His | Pro | Pro |
|     |     |     | 355 |     |     |     | 360 |     |     |     | 365 |     |     |     |     |
|     | Leu | Glu | Ala | Ser | Ile | Ala | Ala | Glu | Lys | Val | Arg | Lys | Tyr | Met | Tyr | Ile |
|     |     | 370 |     |     |     | 375 |     |     |     | 380 |     |     |     |     |     |
|     | Gly | Lys | Gln | Leu | Lys | Phe | Asp | Thr | Ile | Asn | Lys | Cys | His | Ala | Ile | Phe |
|     | 385 |     |     |     | 390 |     |     |     | 395 |     |     |     |     | 400 |     |
|     | Cys | Thr | Ile | Ile | Ile | Asn | Gly | Tyr | Arg | Glu | Arg | His | Gly | Gly | Gln | Trp |
|     |     |     |     | 405 |     |     |     | 410 |     |     |     | 415 |     |     |     |
|     | Pro | Pro | Val | Thr | Leu | Pro | Asp | His | Ala | His | Glu | Phe | Ile | Ile | Asn | Ala |
|     |     |     | 420 |     |     |     | 425 |     |     |     | 430 |     |     |     |     |

```
Tyr  Gly  Ser  Asn  Ser  Ala  Ile  Ser  Tyr  Glu  Asn  Ala  Val  Asp  Tyr  Tyr
          435                     440                     445

Gln  Ser  Phe  Ile  Gly  Ile  Lys  Phe  Asn  Lys  Phe  Ile  Glu  Pro  Gln  Leu
     450                     455                     460

Asp  Glu  Asp  Leu  Thr  Ile  Tyr  Met  Lys  Asp  Lys  Ala  Leu  Ser  Pro  Lys
465                      470                     475                     480

Lys  Ser  Asn  Trp  Asp  Thr  Val  Tyr  Pro  Ala  Ser  Asn  Leu  Leu  Tyr  Arg
                    485                     490                     495

Thr  Asn  Ala  Ser  Asn  Glu  Ser  Arg  Arg  Leu  Val  Glu  Val  Phe  Ile  Ala
               500                     505                     510

Asp  Ser  Lys  Phe  Asp  Pro  His  Gln  Ile  Leu  Asp  Tyr  Val  Glu  Ser  Gly
          515                     520                     525

Asp  Trp  Leu  Asp  Asp  Pro  Glu  Phe  Asn  Ile  Ser  Tyr  Ser  Leu  Lys  Glu
     530                     535                     540

Lys  Glu  Ile  Lys  Gln  Glu  Gly  Arg  Leu  Phe  Ala  Lys  Met  Thr  Tyr  Lys
545                     550                     555                     560

Met  Arg  Ala  Thr  Gln  Val  Leu  Ser  Glu  Thr  Leu  Leu  Ala  Asn  Asn  Ile
               565                     570                     575

Gly  Lys  Phe  Phe  Gln  Glu  Asn  Gly  Met  Val  Lys  Gly  Glu  Ile  Glu  Leu
          580                     585                     590

Leu  Lys  Arg  Leu  Thr  Thr  Ile  Ser  Ile  Ser  Gly  Val  Pro  Arg  Tyr  Asn
          595                     600                     605

Glu  Val  Tyr  Asn  Asn  Ser  Lys  Ser  His  Thr  Asp  Asp  Leu  Lys  Thr  Tyr
     610                     615                     620

Asn  Lys  Ile  Ser  Asn  Leu  Asn  Leu  Ser  Ser  Asn  Gln  Lys  Ser  Lys  Lys
625                     630                     635                     640

Phe  Glu  Phe  Lys  Ser  Thr  Asp  Ile  Tyr  Asn  Asp  Gly  Tyr  Glu  Thr  Val
                    645                     650                     655

Ser  Cys  Phe  Leu  Thr  Thr  Asp  Leu  Lys  Lys  Tyr  Cys  Leu  Asn  Trp  Arg
               660                     665                     670

Tyr  Glu  Ser  Thr  Ala  Leu  Phe  Gly  Glu  Thr  Cys  Asn  Gln  Ile  Phe  Gly
          675                     680                     685

Leu  Asn  Lys  Leu  Phe  Asn  Trp  Leu  His  Pro  Arg  Leu  Glu  Gly  Ser  Thr
     690                     695                     700

Ile  Tyr  Val  Gly  Asp  Pro  Tyr  Cys  Pro  Pro  Ser  Asp  Lys  Glu  His  Ile
705                     710                     715                     720

Ser  Leu  Glu  Asp  His  Pro  Asp  Ser  Gly  Phe  Tyr  Val  His  Asn  Pro  Arg
                    725                     730                     735

Gly  Gly  Ile  Glu  Gly  Phe  Cys  Gln  Lys  Leu  Trp  Thr  Leu  Ile  Ser  Ile
               740                     745                     750

Ser  Ala  Ile  His  Leu  Ala  Ala  Val  Arg  Ile  Gly  Val  Arg  Val  Thr  Ala
          755                     760                     765

Met  Val  Gln  Gly  Asp  Asn  Gln  Ala  Ile  Ala  Val  Thr  Thr  Arg  Val  Pro
     770                     775                     780

Asn  Asn  Tyr  Asp  Tyr  Arg  Val  Lys  Lys  Glu  Ile  Val  Tyr  Lys  Asp  Val
785                     790                     795                     800

Val  Arg  Phe  Phe  Asp  Ser  Leu  Arg  Glu  Val  Met  Asp  Asp  Leu  Gly  His
                    805                     810                     815

Glu  Leu  Lys  Leu  Asn  Glu  Thr  Ile  Ile  Ser  Ser  Lys  Met  Phe  Ile  Tyr
               820                     825                     830

Ser  Lys  Arg  Ile  Tyr  Tyr  Asp  Gly  Arg  Ile  Leu  Pro  Gln  Ala  Leu  Lys
          835                     840                     845

Ala  Leu  Ser  Arg  Cys  Val  Phe  Trp  Ser  Glu  Thr  Val  Ile  Asp  Glu  Thr
          850                     855                     860
```

```
Arg  Ser  Ala  Ser  Ser  Asn  Leu  Ala  Thr  Ser  Phe  Ala  Lys  Ala  Ile  Glu
865                 870                 875                 880

Asn  Gly  Tyr  Ser  Pro  Val  Leu  Gly  Tyr  Ala  Cys  Ser  Ile  Phe  Lys  Asn
                    885                 890                 895

Ile  Gln  Gln  Leu  Tyr  Ile  Ala  Leu  Gly  Met  Asn  Ile  Asn  Pro  Thr  Ile
               900                 905                 910

Thr  Gln  Asn  Ile  Arg  Asp  Gln  Tyr  Phe  Arg  Asn  Pro  Asn  Trp  Met  Gln
          915                 920                 925

Tyr  Ala  Ser  Leu  Ile  Pro  Ala  Ser  Val  Gly  Gly  Phe  Asn  Tyr  Met  Ala
930                 935                 940

Met  Ser  Arg  Cys  Phe  Val  Arg  Asn  Ile  Gly  Asp  Pro  Ser  Val  Ala  Ala
945                 950                 955                 960

Leu  Ala  Asp  Ile  Lys  Arg  Phe  Ile  Lys  Ala  Asn  Leu  Leu  Asp  Arg  Ser
               965                 970                 975

Val  Leu  Tyr  Arg  Ile  Met  Asn  Gln  Glu  Pro  Gly  Glu  Ser  Ser  Phe  Leu
               980                 985                 990

Asp  Trp  Ala  Ser  Asp  Pro  Tyr  Ser  Cys  Asn  Leu  Pro  Gln  Ser  Gln  Asn
          995                 1000                1005

Ile  Thr  Thr  Met  Ile  Lys  Asn  Ile  Thr  Ala  Arg  Asn  Val  Leu  Gln  Asp
     1010                1015                1020

Ser  Pro  Asn  Pro  Leu  Leu  Ser  Gly  Leu  Phe  Thr  Asn  Thr  Met  Ile  Glu
1025                1030                1035                1040

Glu  Asp  Glu  Glu  Leu  Ala  Glu  Phe  Leu  Met  Asp  Arg  Lys  Val  Ile  Leu
                    1045                1050                1055

Pro  Arg  Val  Ala  His  Asp  Ile  Leu  Asp  Asn  Ser  Leu  Thr  Gly  Ile  Arg
               1060                1065                1070

Asn  Ala  Ile  Ala  Gly  Met  Leu  Asp  Thr  Thr  Lys  Ser  Leu  Ile  Arg  Val
          1075                1080                1085

Gly  Ile  Asn  Arg  Gly  Gly  Leu  Thr  Tyr  Ser  Leu  Leu  Arg  Lys  Ile  Ser
     1090                1095                1100

Asn  Tyr  Asp  Leu  Val  Gln  Tyr  Glu  Thr  Leu  Ser  Arg  Thr  Leu  Arg  Leu
1105                1110                1115                1120

Ile  Val  Ser  Asp  Lys  Ile  Lys  Tyr  Glu  Asp  Met  Cys  Ser  Val  Asp  Leu
                    1125                1130                1135

Ala  Ile  Ala  Leu  Arg  Gln  Lys  Met  Trp  Ile  His  Leu  Ser  Gly  Gly  Arg
               1140                1145                1150

Met  Ile  Ser  Gly  Leu  Glu  Thr  Pro  Asp  Pro  Leu  Glu  Leu  Leu  Ser  Gly
          1155                1160                1165

Val  Val  Ile  Thr  Gly  Ser  Glu  His  Cys  Lys  Ile  Cys  Tyr  Ser  Ser  Asp
     1170                1175                1180

Gly  Thr  Asn  Pro  Tyr  Thr  Trp  Met  Tyr  Leu  Pro  Gly  Asn  Ile  Lys  Ile
1185                1190                1195                1200

Gly  Ser  Ala  Glu  Thr  Gly  Ile  Ser  Ser  Leu  Arg  Val  Pro  Tyr  Phe  Gly
                    1205                1210                1215

Ser  Val  Thr  Asp  Glu  Arg  Ser  Glu  Ala  Gln  Leu  Gly  Tyr  Ile  Lys  Asn
               1220                1225                1230

Leu  Ser  Lys  Pro  Ala  Lys  Ala  Ala  Ile  Arg  Ile  Ala  Met  Ile  Tyr  Thr
          1235                1240                1245

Trp  Ala  Phe  Gly  Asn  Asp  Glu  Ile  Ser  Trp  Met  Glu  Ala  Ser  Gln  Ile
     1250                1255                1260

Ala  Gln  Thr  Arg  Ala  Asn  Phe  Thr  Leu  Asp  Ser  Leu  Lys  Ile  Leu  Thr
1265                1270                1275                1280

Pro  Val  Ala  Thr  Ser  Thr  Asn  Leu  Ser  His  Arg  Leu  Lys  Asp  Thr  Ala
```

```
                              1285                    1290                    1295
    Thr  Gln  Met  Lys  Phe  Ser  Ser  Thr  Ser  Leu  Ile  Arg  Val  Ser  Arg  Phe
                        1300                    1305                    1310

Ile  Thr  Met  Ser  Asn  Asp  Asn  Met  Ser  Ile  Lys  Glu  Ala  Asn  Glu  Thr
                        1315                    1320                    1325

Lys  Asp  Thr  Asn  Leu  Ile  Tyr  Gln  Gln  Ile  Met  Leu  Thr  Gly  Leu  Ser
                        1330                    1335                    1340

Val  Phe  Glu  Tyr  Leu  Phe  Arg  Leu  Lys  Glu  Thr  Thr  Gly  His  Asn  Pro
    1345                    1350                    1355                    1360

Ile  Val  Met  His  Leu  His  Ile  Glu  Asp  Glu  Cys  Cys  Ile  Lys  Glu  Ser
                        1365                    1370                    1375

Phe  Asn  Asp  Glu  His  Ile  Asn  Pro  Glu  Ser  Thr  Leu  Glu  Leu  Ile  Arg
                        1380                    1385                    1390

Tyr  Pro  Glu  Ser  Asn  Glu  Phe  Ile  Tyr  Asp  Lys  Asp  Pro  Leu  Lys  Asp
                        1395                    1400                    1405

Val  Asp  Leu  Ser  Lys  Leu  Met  Val  Ile  Lys  Asp  His  Ser  Tyr  Thr  Ile
                        1410                    1415                    1420

Asp  Met  Asn  Tyr  Trp  Asp  Asp  Thr  Asp  Ile  Ile  His  Ala  Ile  Ser  Ile
    1425                    1430                    1435                    1440

Cys  Thr  Ala  Ile  Thr  Ile  Ala  Asp  Thr  Met  Ser  Gln  Leu  Asp  Arg  Asp
                        1445                    1450                    1455

Asn  Leu  Lys  Glu  Ile  Ile  Val  Ile  Ala  Asn  Asp  Asp  Asp  Ile  Asn  Ser
                        1460                    1465                    1470

Leu  Ile  Thr  Glu  Phe  Leu  Thr  Leu  Asp  Ile  Leu  Val  Phe  Leu  Lys  Thr
                        1475                    1480                    1485

Phe  Gly  Gly  Leu  Leu  Val  Asn  Gln  Phe  Ala  Tyr  Thr  Leu  Tyr  Ser  Leu
                        1490                    1495                    1500

Lys  Ile  Glu  Gly  Arg  Asp  Leu  Ile  Trp  Asp  Tyr  Ile  Met  Arg  Thr  Leu
    1505                    1510                    1515                    1520

Arg  Asp  Thr  Ser  His  Ser  Ile  Leu  Lys  Val  Leu  Ser  Asn  Ala  Leu  Ser
                        1525                    1530                    1535

His  Pro  Lys  Val  Phe  Lys  Arg  Phe  Trp  Asp  Cys  Gly  Val  Leu  Asn  Pro
                        1540                    1545                    1550

Ile  Tyr  Gly  Pro  Asn  Thr  Ala  Ser  Gln  Asp  Gln  Ile  Lys  Leu  Ala  Leu
                        1555                    1560                    1565

Ser  Ile  Cys  Glu  Tyr  Ser  Leu  Asp  Leu  Phe  Met  Arg  Glu  Trp  Leu  Asn
                        1570                    1575                    1580

Gly  Val  Ser  Leu  Glu  Ile  Tyr  Ile  Cys  Asp  Ser  Asp  Met  Glu  Val  Ala
    1585                    1590                    1595                    1600

Asn  Asp  Arg  Lys  Gln  Ala  Phe  Ile  Ser  Arg  His  Leu  Ser  Phe  Val  Cys
                        1605                    1610                    1615

Cys  Leu  Ala  Glu  Ile  Ala  Ser  Phe  Gly  Pro  Asn  Leu  Leu  Asn  Leu  Thr
                        1620                    1625                    1630

Tyr  Leu  Glu  Arg  Leu  Asp  Leu  Leu  Lys  Gln  Tyr  Leu  Glu  Leu  Asn  Ile
                        1635                    1640                    1645

Lys  Glu  Asp  Pro  Thr  Leu  Lys  Tyr  Val  Gln  Ile  Ser  Gly  Leu  Leu  Ile
                        1650                    1655                    1660

Lys  Ser  Phe  Pro  Ser  Thr  Val  Thr  Tyr  Val  Arg  Lys  Thr  Ala  Ile  Lys
    1665                    1670                    1675                    1680

Tyr  Leu  Arg  Ile  Arg  Gly  Ile  Ser  Pro  Pro  Glu  Val  Ile  Asp  Asp  Trp
                        1685                    1690                    1695

Asp  Pro  Val  Glu  Asp  Glu  Asn  Met  Leu  Asp  Asn  Ile  Val  Lys  Thr  Ile
                        1700                    1705                    1710
```

```
Asn  Asp  Asn  Cys  Asn  Lys  Asp  Asn  Lys  Gly  Asn  Lys  Ile  Asn  Asn  Phe
          1715                1720                     1725

Trp  Gly  Leu  Ala  Leu  Lys  Asn  Tyr  Gln  Val  Leu  Lys  Ile  Arg  Ser  Ile
          1730                1735                     1740

Thr  Ser  Asp  Ser  Asp  Asp  Asn  Asp  Arg  Leu  Asp  Ala  Asn  Thr  Ser  Gly
1745                     1750                     1755                     1760

Leu  Thr  Leu  Pro  Gln  Gly  Gly  Asn  Tyr  Leu  Ser  His  Gln  Leu  Arg  Leu
                    1765                     1770                     1775

Phe  Gly  Ile  Asn  Ser  Thr  Ser  Cys  Leu  Lys  Ala  Leu  Glu  Leu  Ser  Gln
               1780                     1785                     1790

Ile  Leu  Met  Lys  Glu  Val  Asn  Lys  Asp  Lys  Asp  Arg  Leu  Phe  Leu  Gly
          1795                1800                     1805

Glu  Gly  Ala  Gly  Ala  Met  Leu  Ala  Cys  Tyr  Asp  Ala  Thr  Leu  Gly  Pro
          1810                1815                     1820

Ala  Val  Asn  Tyr  Tyr  Asn  Ser  Gly  Leu  Asn  Ile  Thr  Asp  Val  Ile  Gly
1825                     1830                     1835                     1840

Gln  Arg  Glu  Leu  Lys  Ile  Phe  Pro  Ser  Glu  Val  Ser  Leu  Val  Gly  Lys
                    1845                     1850                     1855

Lys  Leu  Gly  Asn  Val  Thr  Gln  Ile  Leu  Asn  Arg  Val  Lys  Val  Leu  Phe
               1860                     1865                     1870

Asn  Gly  Asn  Pro  Asn  Ser  Thr  Trp  Ile  Gly  Asn  Met  Glu  Cys  Glu  Ser
          1875                1880                     1885

Leu  Ile  Trp  Ser  Glu  Leu  Asn  Asp  Lys  Ser  Ile  Gly  Leu  Val  His  Cys
          1890                1895                     1900

Asp  Met  Glu  Gly  Ala  Ile  Gly  Lys  Ser  Glu  Glu  Thr  Val  Leu  His  Glu
1905                     1910                     1915                     1920

His  Tyr  Ser  Val  Ile  Arg  Ile  Thr  Tyr  Leu  Ile  Gly  Asp  Asp  Asp  Val
                    1925                     1930                     1935

Val  Leu  Val  Ser  Lys  Ile  Ile  Pro  Thr  Ile  Thr  Pro  Asn  Trp  Ser  Arg
               1940                     1945                     1950

Ile  Leu  Tyr  Leu  Tyr  Lys  Leu  Tyr  Trp  Lys  Asp  Val  Ser  Ile  Ile  Ser
               1955                     1960                     1965

Leu  Lys  Thr  Ser  Asn  Pro  Ala  Ser  Thr  Glu  Leu  Tyr  Leu  Ile  Ser  Lys
          1970                1975                     1980

Asp  Ala  Tyr  Cys  Thr  Ile  Met  Glu  Pro  Ser  Glu  Ile  Val  Leu  Ser  Lys
1985                     1990                     1995                     2000

Leu  Lys  Arg  Leu  Ser  Leu  Leu  Glu  Glu  Asn  Asn  Leu  Leu  Lys  Trp  Ile
                    2005                     2010                     2015

Ile  Leu  Ser  Lys  Lys  Arg  Asn  Asn  Glu  Trp  Leu  His  His  Glu  Ile  Lys
               2020                     2025                     2030

Glu  Gly  Glu  Arg  Asp  Tyr  Gly  Ile  Met  Arg  Pro  Tyr  His  Met  Ala  Leu
          2035                2040                     2045

Gln  Ile  Phe  Gly  Phe  Gln  Ile  Asn  Leu  Asn  His  Leu  Ala  Lys  Glu  Phe
          2050                2055                     2060

Leu  Ser  Thr  Pro  Asp  Leu  Thr  Asn  Ile  Asn  Asn  Ile  Ile  Gln  Ser  Phe
2065                     2070                     2075                     2080

Gln  Arg  Thr  Ile  Lys  Asp  Val  Leu  Phe  Glu  Trp  Ile  Asn  Ile  Thr  His
                    2085                     2090                     2095

Asp  Asp  Lys  Arg  His  Lys  Leu  Gly  Gly  Arg  Tyr  Asn  Ile  Phe  Pro  Leu
                    2100                     2105                     2110

Lys  Asn  Lys  Gly  Lys  Leu  Arg  Leu  Leu  Ser  Arg  Arg  Leu  Val  Leu  Ser
               2115                     2120                     2125

Trp  Ile  Ser  Leu  Ser  Leu  Ser  Thr  Arg  Leu  Leu  Thr  Gly  Arg  Phe  Pro
          2130                2135                     2140
```

Asp Glu Lys Phe Glu His Arg Ala Gln Thr Gly Tyr Val Ser Leu Ala
2145                2150                2155                2160

Asp Thr Asp Leu Glu Ser Leu Lys Leu Leu Ser Lys Asn Ile Ile Lys
            2165                2170                2175

Asn Tyr Arg Glu Cys Ile Gly Ser Ile Ser Tyr Trp Phe Leu Thr Lys
            2180                2185                2190

Glu Val Lys Ile Leu Met Lys Leu Ile Gly Gly Ala Lys Leu Leu Gly
        2195            2200                2205

Ile Pro Arg Gln Tyr Lys Glu Pro Glu Asp Gln Leu Leu Glu Asn Tyr
        2210            2215                2220

Asn Gln His Asp Glu Phe Asp Ile Asp
2225                2230

(2) INFORMATION FOR SEQ ID NO:2:

(i) SEQUENCE CHARACTERISTICS:
        (A) LENGTH: 2233 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Human parainfluenza virus 3
        (B) STRAIN: cp45

(xi) SEQUENCE DESCRIPTION: SEQ ID NO:2:

Met Asp Thr Glu Ser Asn Asn Gly Thr Val Ser Asp Ile Leu Tyr Pro
1               5                   10              15

Glu Cys His Leu Asn Ser Pro Ile Val Lys Gly Lys Ile Ala Gln Leu
            20              25              30

His Thr Ile Met Ser Leu Pro Gln Pro Tyr Asp Met Asp Asp Ser
            35              40              45

Ile Leu Val Ile Thr Arg Gln Lys Ile Lys Leu Asn Lys Leu Asp Lys
        50              55              60

Arg Gln Arg Ser Ile Arg Arg Leu Lys Leu Ile Leu Thr Glu Lys Val
65              70              75              80

Asn Asp Leu Gly Lys Tyr Thr Phe Ile Arg Tyr Pro Glu Met Ser Lys
            85              90              95

Glu Met Phe Lys Leu Tyr Ile Pro Gly Ile Asn Ser Lys Val Thr Glu
            100             105             110

Leu Leu Leu Lys Ala Asp Arg Thr Tyr Ser Gln Met Thr Asp Gly Leu
        115             120             125

Arg Asp Leu Trp Ile Asn Val Leu Ser Lys Leu Ala Ser Lys Asn Asp
        130             135             140

Gly Ser Asn Tyr Asp Leu Asn Glu Glu Ile Asn Asn Ile Ser Lys Val
145             150             155             160

His Thr Thr Tyr Lys Ser Asp Lys Trp Tyr Asn Pro Phe Lys Thr Trp
            165             170             175

Phe Thr Ile Lys Tyr Asp Met Arg Arg Leu Gln Lys Ala Arg Asn Glu
            180             185             190

Ile Thr Phe Asn Val Gly Lys Asp Tyr Asn Leu Leu Glu Asp Gln Lys
        195             200             205

Asn Phe Leu Leu Ile His Pro Glu Leu Val Leu Ile Leu Asp Lys Gln
        210             215             220

Asn Tyr Asn Gly Tyr Leu Ile Thr Pro Glu Leu Val Leu Met Tyr Cys
225             230             235             240

-continued

```
Asp  Val  Val  Glu  Gly  Arg  Trp  Asn  Ile  Ser  Ala  Cys  Ala  Lys  Leu  Asp
              245                     250                         255

Pro  Lys  Leu  Gln  Ser  Met  Tyr  Gln  Lys  Gly  Asn  Asn  Leu  Trp  Glu  Val
              260                     265                         270

Ile  Asp  Lys  Leu  Phe  Pro  Ile  Met  Gly  Glu  Lys  Thr  Phe  Asp  Val  Ile
              275                     280                         285

Ser  Leu  Leu  Glu  Pro  Leu  Ala  Leu  Ser  Leu  Ile  Gln  Thr  His  Asp  Pro
              290                     295                         300

Val  Lys  Gln  Leu  Arg  Gly  Ala  Phe  Leu  Asn  His  Val  Leu  Ser  Glu  Met
305                     310                     315                         320

Glu  Leu  Ile  Phe  Glu  Ser  Arg  Glu  Ser  Ile  Lys  Glu  Phe  Leu  Ser  Val
              325                     330                         335

Asp  Tyr  Ile  Asp  Lys  Ile  Leu  Asp  Ile  Phe  Asn  Lys  Ser  Thr  Ile  Asp
              340                     345                         350

Glu  Ile  Ala  Glu  Ile  Phe  Ser  Phe  Phe  Arg  Thr  Phe  Gly  His  Pro  Pro
              355                     360                         365

Leu  Glu  Ala  Ser  Ile  Ala  Ala  Glu  Lys  Val  Arg  Lys  Tyr  Met  Tyr  Ile
              370                     375                         380

Gly  Lys  Gln  Leu  Lys  Phe  Asp  Thr  Ile  Asn  Lys  Cys  His  Ala  Ile  Phe
385                     390                     395                         400

Cys  Thr  Ile  Ile  Ile  Asn  Gly  Tyr  Arg  Glu  Arg  His  Gly  Gly  Gln  Trp
              405                     410                         415

Pro  Pro  Val  Thr  Leu  Pro  Asp  His  Ala  His  Glu  Phe  Ile  Ile  Asn  Ala
              420                     425                         430

Tyr  Gly  Ser  Asn  Ser  Ala  Ile  Ser  Tyr  Glu  Asn  Ala  Val  Asp  Tyr  Tyr
              435                     440                         445

Gln  Ser  Phe  Ile  Gly  Ile  Lys  Phe  Asn  Lys  Phe  Ile  Glu  Pro  Gln  Leu
              450                     455                         460

Asp  Glu  Asp  Leu  Thr  Ile  Tyr  Met  Lys  Asp  Lys  Ala  Leu  Ser  Pro  Lys
465                     470                     475                         480

Lys  Ser  Asn  Trp  Asp  Thr  Val  Tyr  Pro  Ala  Ser  Asn  Leu  Leu  Tyr  Arg
              485                     490                         495

Thr  Asn  Ala  Ser  Asn  Glu  Ser  Arg  Arg  Leu  Val  Glu  Val  Phe  Ile  Ala
              500                     505                         510

Asp  Ser  Lys  Phe  Asp  Pro  His  Gln  Ile  Leu  Asp  Tyr  Val  Glu  Ser  Gly
              515                     520                         525

Asp  Trp  Leu  Asp  Asp  Pro  Glu  Phe  Asn  Ile  Ser  Tyr  Ser  Leu  Lys  Glu
              530                     535                         540

Lys  Glu  Ile  Lys  Gln  Glu  Gly  Arg  Leu  Phe  Ala  Lys  Met  Thr  Tyr  Lys
545                     550                     555                         560

Met  Arg  Ala  Thr  Gln  Val  Leu  Ser  Glu  Thr  Leu  Leu  Ala  Asn  Asn  Ile
              565                     570                         575

Gly  Lys  Phe  Phe  Gln  Glu  Asn  Gly  Met  Val  Lys  Gly  Glu  Ile  Glu  Leu
              580                     585                         590

Leu  Lys  Arg  Leu  Thr  Thr  Ile  Ser  Ile  Ser  Gly  Val  Pro  Arg  Tyr  Asn
              595                     600                         605

Glu  Val  Tyr  Asn  Asn  Ser  Lys  Ser  His  Thr  Asp  Asp  Leu  Lys  Thr  Tyr
              610                     615                         620

Asn  Lys  Ile  Ser  Asn  Leu  Asn  Leu  Ser  Ser  Asn  Gln  Lys  Ser  Lys  Lys
625                     630                     635                         640

Phe  Glu  Phe  Lys  Ser  Thr  Asp  Ile  Tyr  Asn  Asp  Gly  Tyr  Glu  Thr  Val
              645                     650                         655

Ser  Cys  Phe  Leu  Thr  Thr  Asp  Leu  Lys  Lys  Tyr  Cys  Leu  Asn  Trp  Arg
```

-continued

|  |  |  | 660 |  |  |  |  | 665 |  |  |  |  | 670 |  |
|---|---|---|---|---|---|---|---|---|---|---|---|---|---|---|
| Tyr | Glu | Ser<br>675 | Thr | Ala | Leu | Phe | Gly<br>680 | Thr | Cys | Asn | Gln<br>685 | Ile | Phe | Gly |
| Leu | Asn | Lys<br>690 | Leu | Phe | Asn | Trp | Leu<br>695 | His | Pro | Arg | Leu<br>700 | Glu | Gly | Ser | Thr |
| Ile | Tyr | Val<br>705 | Gly | Asp | Pro<br>710 | Tyr | Cys | Pro | Pro | Ser<br>715 | Asp | Lys | Glu | His | Ile<br>720 |
| Ser | Leu | Glu | Asp | His<br>725 | Pro | Asp | Ser | Gly | Phe<br>730 | Tyr | Val | His | Asn | Pro<br>735 | Arg |
| Gly | Gly | Ile | Glu<br>740 | Gly | Phe | Cys | Gln | Lys<br>745 | Leu | Trp | Thr | Leu | Ile<br>750 | Ser | Ile |
| Ser | Ala | Ile<br>755 | His | Leu | Ala | Ala | Val<br>760 | Arg | Ile | Gly | Val<br>765 | Arg | Val | Thr | Ala |
| Met | Val<br>770 | Gln | Gly | Asp | Asn | Gln<br>775 | Ala | Ile | Ala | Val | Thr<br>780 | Thr | Arg | Val | Pro |
| Asn<br>785 | Asn | Tyr | Asp | Tyr | Arg<br>790 | Val | Lys | Lys | Glu | Ile<br>795 | Val | Tyr | Lys | Asp | Val<br>800 |
| Val | Arg | Phe | Phe | Asp<br>805 | Ser | Leu | Arg | Glu | Val<br>810 | Met | Asp | Asp | Leu | Gly<br>815 | His |
| Glu | Leu | Lys | Leu<br>820 | Asn | Glu | Thr | Ile | Ile<br>825 | Ser | Ser | Lys | Met | Phe<br>830 | Ile | Tyr |
| Ser | Lys | Arg<br>835 | Ile | Tyr | Tyr | Asp | Gly<br>840 | Arg | Ile | Leu | Pro | Gln<br>845 | Ala | Leu | Lys |
| Ala | Leu | Ser<br>850 | Arg | Cys | Val | Phe | Trp<br>855 | Ser | Glu | Thr | Val | Ile<br>860 | Asp | Glu | Thr |
| Arg<br>865 | Ser | Ala | Ser | Ser | Asn<br>870 | Leu | Ala | Thr | Ser | Phe<br>875 | Ala | Lys | Ala | Ile | Glu<br>880 |
| Asn | Gly | Tyr | Ser | Pro<br>885 | Val | Leu | Gly | Tyr | Ala<br>890 | Cys | Ser | Ile | Phe | Lys<br>895 | Asn |
| Ile | Gln | Gln | Leu<br>900 | Tyr | Ile | Ala | Leu | Gly<br>905 | Met | Asn | Ile | Asn | Pro<br>910 | Thr | Ile |
| Thr | Gln | Asn<br>915 | Ile | Arg | Asp | Gln | Tyr<br>920 | Phe | Arg | Asn | Pro | Asn<br>925 | Trp | Met | Gln |
| Tyr | Ala<br>930 | Ser | Leu | Ile | Pro | Ala<br>935 | Ser | Val | Gly | Gly | Phe<br>940 | Asn | His | Met | Ala |
| Met<br>945 | Ser | Arg | Cys | Phe | Val<br>950 | Arg | Asn | Ile | Gly | Asp<br>955 | Pro | Ser | Val | Ala | Ala<br>960 |
| Leu | Ala | Asp | Ile | Lys<br>965 | Arg | Phe | Ile | Lys | Ala<br>970 | Asn | Leu | Leu | Asp | Arg<br>975 | Ser |
| Val | Leu | Tyr | Arg<br>980 | Ile | Met | Asn | Gln | Glu<br>985 | Pro | Gly | Glu | Ser | Ser<br>990 | Phe | Phe |
| Asp | Trp | Ala<br>995 | Ser | Asp | Pro | Tyr | Ser<br>1000 | Cys | Asn | Leu | Pro | Gln<br>1005 | Ser | Gln | Asn |
| Ile | Thr | Thr | Met<br>1010 | Ile | Lys | Asn | Ile | Thr<br>1015 | Ala | Arg | Asn | Val<br>1020 | Leu | Gln | Asp |
| Ser<br>1025 | Pro | Asn | Pro | Leu | Leu<br>1030 | Ser | Gly | Leu | Phe | Thr<br>1035 | Asn | Thr | Met | Ile | Glu<br>1040 |
| Glu | Asp | Glu | Glu | Leu<br>1045 | Ala | Glu | Phe | Leu | Met<br>1050 | Asp | Arg | Lys | Val | Ile<br>1055 | Leu |
| Pro | Arg | Val | Ala | His<br>1060 | Asp | Ile | Leu | Asp | Asn<br>1065 | Ser | Leu | Thr | Gly | Ile<br>1070 | Arg |
| Asn | Ala | Ile<br>1075 | Ala | Gly | Met | Leu | Asp<br>1080 | Thr | Thr | Lys | Ser | Leu<br>1085 | Ile | Arg | Val |

```
Gly  Ile  Asn  Arg  Gly  Gly  Leu  Thr  Tyr  Ser  Leu  Leu  Arg  Lys  Ile  Ser
     1090                1095                          1100

Asn  Tyr  Asp  Leu  Val  Gln  Tyr  Glu  Thr  Leu  Ser  Arg  Thr  Leu  Arg  Leu
1105                1110                     1115                          1120

Ile  Val  Ser  Asp  Lys  Ile  Lys  Tyr  Glu  Asp  Met  Cys  Ser  Val  Asp  Leu
               1125                     1130                          1135

Ala  Ile  Ala  Leu  Arg  Gln  Lys  Met  Trp  Ile  His  Leu  Ser  Gly  Gly  Arg
               1140                     1145                          1150

Met  Ile  Ser  Gly  Leu  Glu  Thr  Pro  Asp  Pro  Leu  Glu  Leu  Leu  Ser  Gly
          1155                1160                          1165

Val  Val  Ile  Thr  Gly  Ser  Glu  His  Cys  Lys  Ile  Cys  Tyr  Ser  Ser  Asp
               1170                1175                     1180

Gly  Thr  Asn  Pro  Tyr  Thr  Trp  Met  Tyr  Leu  Pro  Gly  Asn  Ile  Lys  Ile
1185                     1190                     1195                     1200

Gly  Ser  Ala  Glu  Thr  Gly  Ile  Ser  Ser  Leu  Arg  Val  Pro  Tyr  Phe  Gly
                    1205                     1210                     1215

Ser  Val  Thr  Asp  Glu  Arg  Ser  Glu  Ala  Gln  Leu  Gly  Tyr  Ile  Lys  Asn
                    1220                1225                     1230

Leu  Ser  Lys  Pro  Ala  Lys  Ala  Ala  Ile  Arg  Ile  Ala  Met  Ile  Tyr  Thr
               1235                1240                          1245

Trp  Ala  Phe  Gly  Asn  Asp  Glu  Ile  Ser  Trp  Met  Glu  Ala  Ser  Gln  Ile
1250                     1255                     1260

Ala  Gln  Thr  Arg  Ala  Asn  Phe  Thr  Leu  Asp  Ser  Leu  Lys  Ile  Leu  Thr
1265                     1270                     1275                     1280

Pro  Val  Ala  Thr  Ser  Thr  Asn  Leu  Ser  His  Arg  Leu  Lys  Asp  Thr  Ala
                    1285                     1290                     1295

Thr  Gln  Met  Lys  Phe  Ser  Ser  Thr  Ser  Leu  Ile  Arg  Val  Ser  Arg  Phe
               1300                     1305                     1310

Ile  Thr  Met  Ser  Asn  Asp  Asn  Met  Ser  Ile  Lys  Glu  Ala  Asn  Glu  Thr
          1315                     1320                     1325

Lys  Asp  Thr  Asn  Leu  Ile  Tyr  Gln  Gln  Ile  Met  Leu  Thr  Gly  Leu  Ser
          1330                     1335                     1340

Val  Phe  Glu  Tyr  Leu  Phe  Arg  Leu  Lys  Glu  Thr  Thr  Gly  His  Asn  Pro
1345                     1350                     1355                     1360

Ile  Val  Met  His  Leu  His  Ile  Glu  Asp  Glu  Cys  Cys  Ile  Lys  Glu  Ser
                    1365                     1370                     1375

Phe  Asn  Asp  Glu  His  Ile  Asn  Pro  Glu  Ser  Thr  Leu  Glu  Leu  Ile  Arg
               1380                     1385                     1390

Tyr  Pro  Glu  Ser  Asn  Glu  Phe  Ile  Tyr  Asp  Lys  Asp  Pro  Leu  Lys  Asp
               1395                     1400                     1405

Val  Asp  Leu  Ser  Lys  Leu  Met  Val  Ile  Lys  Asp  His  Ser  Tyr  Thr  Ile
1410                     1415                     1420

Asp  Met  Asn  Tyr  Trp  Asp  Asp  Thr  Asp  Ile  Ile  His  Ala  Ile  Ser  Ile
1425                     1430                     1435                     1440

Cys  Thr  Ala  Ile  Thr  Ile  Ala  Asp  Thr  Met  Ser  Gln  Leu  Asp  Arg  Asp
                    1445                     1450                     1455

Asn  Leu  Lys  Glu  Ile  Ile  Val  Ile  Ala  Asn  Asp  Asp  Ile  Asn  Ser
               1460                     1465                     1470

Leu  Ile  Thr  Glu  Phe  Leu  Thr  Leu  Asp  Ile  Leu  Val  Phe  Leu  Lys  Thr
          1475                     1480                     1485

Phe  Gly  Gly  Leu  Leu  Val  Asn  Gln  Phe  Ala  Tyr  Thr  Leu  Tyr  Ser  Leu
          1490                     1495                     1500

Lys  Ile  Glu  Gly  Arg  Asp  Leu  Ile  Trp  Asp  Tyr  Ile  Met  Arg  Thr  Leu
1505                     1510                     1515                     1520
```

```
Arg  Asp  Thr  Ser  His  Ser  Ile  Leu  Lys  Val  Leu  Ser  Asn  Ala  Leu  Ser
               1525                    1530                    1535

His  Pro  Lys  Val  Phe  Lys  Arg  Phe  Trp  Asp  Cys  Gly  Val  Leu  Asn  Pro
               1540                    1545                    1550

Ile  Tyr  Gly  Pro  Asn  Ile  Ala  Ser  Gln  Asp  Gln  Ile  Lys  Leu  Ala  Leu
               1555                    1560                    1565

Ser  Ile  Cys  Glu  Tyr  Ser  Leu  Asp  Leu  Phe  Met  Arg  Glu  Trp  Leu  Asn
               1570                    1575                    1580

Gly  Val  Ser  Leu  Glu  Ile  Tyr  Ile  Cys  Asp  Ser  Asp  Met  Glu  Val  Ala
1585                    1590                    1595                    1600

Asn  Asp  Arg  Lys  Gln  Ala  Phe  Ile  Ser  Arg  His  Leu  Ser  Phe  Val  Cys
               1605                    1610                    1615

Cys  Leu  Ala  Glu  Ile  Ala  Ser  Phe  Gly  Pro  Asn  Leu  Leu  Asn  Leu  Thr
               1620                    1625                    1630

Tyr  Leu  Glu  Arg  Leu  Asp  Leu  Leu  Lys  Gln  Tyr  Leu  Glu  Leu  Asn  Ile
               1635                    1640                    1645

Lys  Glu  Asp  Pro  Thr  Leu  Lys  Tyr  Val  Gln  Ile  Ser  Gly  Leu  Leu  Ile
               1650                    1655                    1660

Lys  Ser  Phe  Pro  Ser  Thr  Val  Thr  Tyr  Val  Arg  Lys  Thr  Ala  Ile  Lys
1665                    1670                    1675                    1680

Tyr  Leu  Arg  Ile  Arg  Gly  Ile  Ser  Pro  Pro  Glu  Val  Ile  Asp  Asp  Trp
               1685                    1690                    1695

Asp  Pro  Val  Glu  Asp  Glu  Asn  Met  Leu  Asp  Asn  Ile  Val  Lys  Thr  Ile
               1700                    1705                    1710

Asn  Asp  Asn  Cys  Asn  Lys  Asp  Asn  Lys  Gly  Asn  Lys  Ile  Asn  Asn  Phe
               1715                    1720                    1725

Trp  Gly  Leu  Ala  Leu  Lys  Asn  Tyr  Gln  Val  Leu  Lys  Ile  Arg  Ser  Ile
               1730                    1735                    1740

Thr  Ser  Asp  Ser  Asp  Asp  Asn  Asp  Arg  Leu  Asp  Ala  Asn  Thr  Ser  Gly
1745                    1750                    1755                    1760

Leu  Thr  Leu  Pro  Gln  Gly  Gly  Asn  Tyr  Leu  Ser  His  Gln  Leu  Arg  Leu
               1765                    1770                    1775

Phe  Gly  Ile  Asn  Ser  Thr  Ser  Cys  Leu  Lys  Ala  Leu  Glu  Leu  Ser  Gln
               1780                    1785                    1790

Ile  Leu  Met  Lys  Glu  Val  Asn  Lys  Asp  Lys  Asp  Arg  Leu  Phe  Leu  Gly
               1795                    1800                    1805

Glu  Gly  Ala  Gly  Ala  Met  Leu  Ala  Cys  Tyr  Asp  Ala  Thr  Leu  Gly  Pro
1810                    1815                    1820

Ala  Val  Asn  Tyr  Tyr  Asn  Ser  Gly  Leu  Asn  Ile  Thr  Asp  Val  Ile  Gly
1825                    1830                    1835                    1840

Gln  Arg  Glu  Leu  Lys  Ile  Phe  Pro  Ser  Glu  Val  Ser  Leu  Val  Gly  Lys
               1845                    1850                    1855

Lys  Leu  Gly  Asn  Val  Thr  Gln  Ile  Leu  Asn  Arg  Val  Lys  Val  Leu  Phe
               1860                    1865                    1870

Asn  Gly  Asn  Pro  Asn  Ser  Thr  Trp  Ile  Gly  Asn  Met  Glu  Cys  Glu  Ser
               1875                    1880                    1885

Leu  Ile  Trp  Ser  Glu  Leu  Asn  Asp  Lys  Ser  Ile  Gly  Leu  Val  His  Cys
               1890                    1895                    1900

Asp  Met  Glu  Gly  Ala  Ile  Gly  Lys  Ser  Glu  Glu  Thr  Val  Leu  His  Glu
1905                    1910                    1915                    1920

His  Tyr  Ser  Val  Ile  Arg  Ile  Thr  Tyr  Leu  Ile  Gly  Asp  Asp  Asp  Val
               1925                    1930                    1935

Val  Leu  Val  Ser  Lys  Ile  Ile  Pro  Thr  Ile  Thr  Pro  Asn  Trp  Ser  Arg
```

-continued

```
                    1940                            1945                            1950
        Ile Leu Tyr Leu Tyr Lys Leu Tyr Trp Lys Asp Val Ser Ile Ile Ser
                    1955                            1960                            1965
        Leu Lys Thr Ser Asn Pro Ala Ser Thr Glu Leu Tyr Leu Ile Ser Lys
                    1970                            1975                            1980
        Asp Ala Tyr Cys Thr Ile Met Glu Pro Ser Glu Ile Val Leu Ser Lys
        1985                            1990                            1995                    2000
        Leu Lys Arg Leu Ser Leu Leu Glu Glu Asn Asn Leu Leu Lys Trp Ile
                                    2005                    2010                            2015
        Ile Leu Ser Lys Lys Arg Asn Asn Glu Trp Leu His His Glu Ile Lys
                            2020                    2025                            2030
        Glu Gly Glu Arg Asp Tyr Gly Ile Met Arg Pro Tyr His Met Ala Leu
                    2035                            2040                            2045
        Gln Ile Phe Gly Phe Gln Ile Asn Leu Asn His Leu Ala Lys Glu Phe
                2050                            2055                            2060
        Leu Ser Thr Pro Asp Leu Thr Asn Ile Asn Asn Ile Ile Gln Ser Phe
        2065                            2070                            2075                    2080
        Gln Arg Thr Ile Lys Asp Val Leu Phe Glu Trp Ile Asn Ile Thr His
                                2085                    2090                            2095
        Asp Asp Lys Arg His Lys Leu Gly Gly Arg Tyr Asn Ile Phe Pro Leu
                            2100                    2105                            2110
        Lys Asn Lys Gly Lys Leu Arg Leu Leu Ser Arg Arg Leu Val Leu Ser
                    2115                    2120                            2125
        Trp Ile Ser Leu Ser Leu Ser Thr Arg Leu Leu Thr Gly Arg Phe Pro
                2130                            2135                            2140
        Asp Glu Lys Phe Glu His Arg Ala Gln Thr Gly Tyr Val Ser Leu Ala
        2145                            2150                            2155                    2160
        Asp Thr Asp Leu Glu Ser Leu Lys Leu Leu Ser Lys Asn Ile Ile Lys
                                2165                            2170                    2175
        Asn Tyr Arg Glu Cys Ile Gly Ser Ile Ser Tyr Trp Phe Leu Thr Lys
                        2180                    2185                            2190
        Glu Val Lys Ile Leu Met Lys Leu Ile Gly Gly Ala Lys Leu Leu Gly
                    2195                    2200                            2205
        Ile Pro Arg Gln Tyr Lys Glu Pro Glu Asp Gln Leu Leu Glu Asn Tyr
                2210                        2215                        2220
        Asn Gln His Asp Glu Phe Asp Ile Asp
        2225                    2230
```